United States Patent [19]

Putter

[11] Patent Number: 4,834,982
[45] Date of Patent: May 30, 1989

[54] POTASSIUM-NEUTRAL SALURETICUM WITH ANTI-HYPERTENSIVE EFFECT

[75] Inventor: Sigurd Putter, Iserlohn, Fed. Rep. of Germany

[73] Assignee: Medice Chem.-Pharm. Fabrik Putter GmbH & Co. KG, Iserlohn, Fed. Rep. of Germany

[21] Appl. No.: 113,747

[22] Filed: Oct. 23, 1987

Related U.S. Application Data

[63] Continuation-in-part of Ser. No. 773,812, Sep. 9, 1985, abandoned, which is a continuation-in-part of Ser. No. 522,037, Aug. 9, 1983, abandoned.

[51] Int. Cl.$^4$ ............................................. A61K 9/54
[52] U.S. Cl. ............................... 424/458; 424/490; 424/497; 424/494; 424/498; 424/470; 424/436; 424/456; 424/476; 424/480; 424/482; 514/869; 514/963
[58] Field of Search ..................... 424/458, 436, 476

[56] References Cited

U.S. PATENT DOCUMENTS

| | | | |
|---|---|---|---|
| 4,217,347 | 8/1980 | Horovitz et al. | 524/222 |
| 4,324,779 | 4/1982 | Dalhausen et al. | 424/476 |
| 4,574,080 | 3/1986 | Roswall et al. | 424/458 |
| 4,590,062 | 5/1986 | Jang | 424/19 |
| 4,695,591 | 9/1987 | Hanna et al. | 424/436 |

Primary Examiner—Thurman K. Page
Assistant Examiner—T. R. Horne
Attorney, Agent, or Firm—Scully, Scott, Murphy & Presser

[57] ABSTRACT

A diuretically active combination comprising furosemide and triamterene in a ratio of 1:1 to 1:2, in which furosemide is in the form of controlled release so as to facilitate solubilization of the furosemide in triamterene micelles to stabilize the combination as mixed micelles of low polydispersity yielding dissolution rates in in vitro tests of furosemide of not more than about 1.5% after about one hour at pH 1.5 to 3.5 and a slow release of not more than about 4.5% at pH 5.5 concurrent with a release of triamterene of about 60–70% and 80%, respectively, and with a release of not more than 85% furosemide after eight hours at pH 7.5 in salt solutions of adjusted pH.

13 Claims, 12 Drawing Sheets

① —·—·— TRIAMTERENE WITHOUT FUROSEMIDE
② — — — FUROSEMIDE, IN SLIGHTLY RELEASED FORM IN THE ABSENCE OF TRIAMTERENE (ACCORDING TO DAHLHAUSEN)
③ ············ REL. SOLUBILITY OF FUROSEMIDE, NORMAL
④ ———— BOUND $^{14}$C-FUROSEMIDE TO TRIAMTERENE, THIS INVENTION
⑤ ———— FUROSEMIDE SOLUBILITY IN THE PRESENCE OF TRIAMTERENE, THIS INVENTION

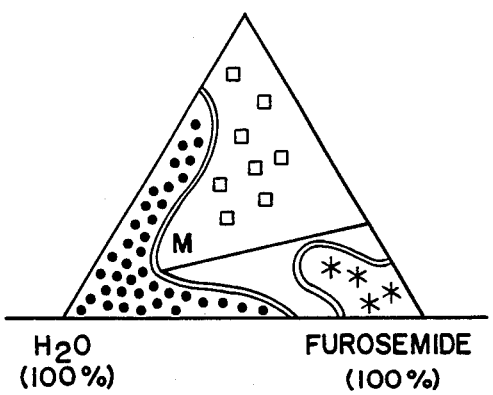

LOOSE COMBINATIONS, VARIATION OF
MOLAR RATIOS RANGING FROM 1:10

- ▫ MOLECULAR DISPERSION
- ✳ MICELLES, LARGE SIZE VARIATION
- • SPHERICAL MICELLES, SMALL-SIZE VARIATION

FIG. 7A

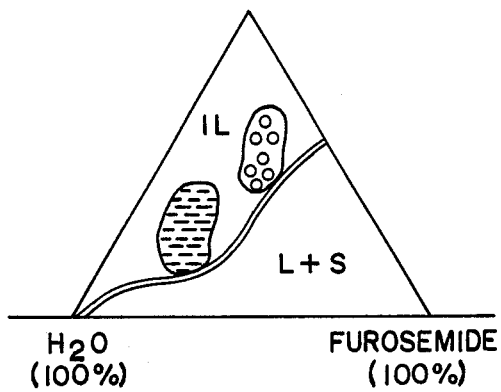

FIXED MOLAR RATIOS, WHERE
FUROSEMIDE IS IN SUSTAINED RELEASE

- ≡ 1:2 RATIO
- ○ 1:1 RATIO
- IL: ISOTROPIC LIQUID
- L+S LIQUID AND CRYSTALLINE

FIG. 7B

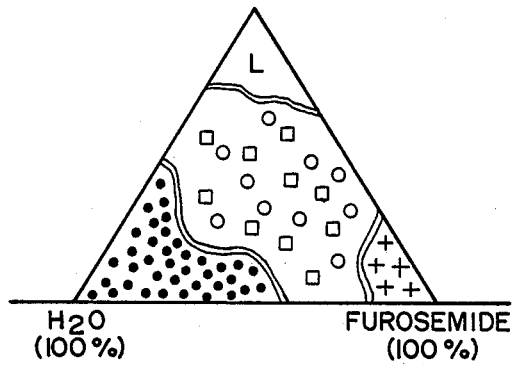

FIXED RATIO; FUROSEMIDE TO TRIAMTERENE FROM
1:0,5; 1:1; 1:2; 1:3; HOWEVER FUROSEMIDE IN NON
SUSTAINED RELEASED FORM

- ▫ MOLECULAR DISPERSION
- ○ MICELLES OF DIFFERENT SIZES, INCLUDING MICROCRYSTALS
- • SMALL SPHERICAL MICELLES OF TRIAMTERENE, DISPERSED IN A WATERY SOLUTION
- L LYOTROPIC PHASE, LIQUID CRYSTALLINE PHASE
- ≈ ISOTROPIC LIQUID BORDERLINES
- +++ LIQUID CRYSTALLINE, LIQUID MEMBRANE FORMATION

FIG. 7C

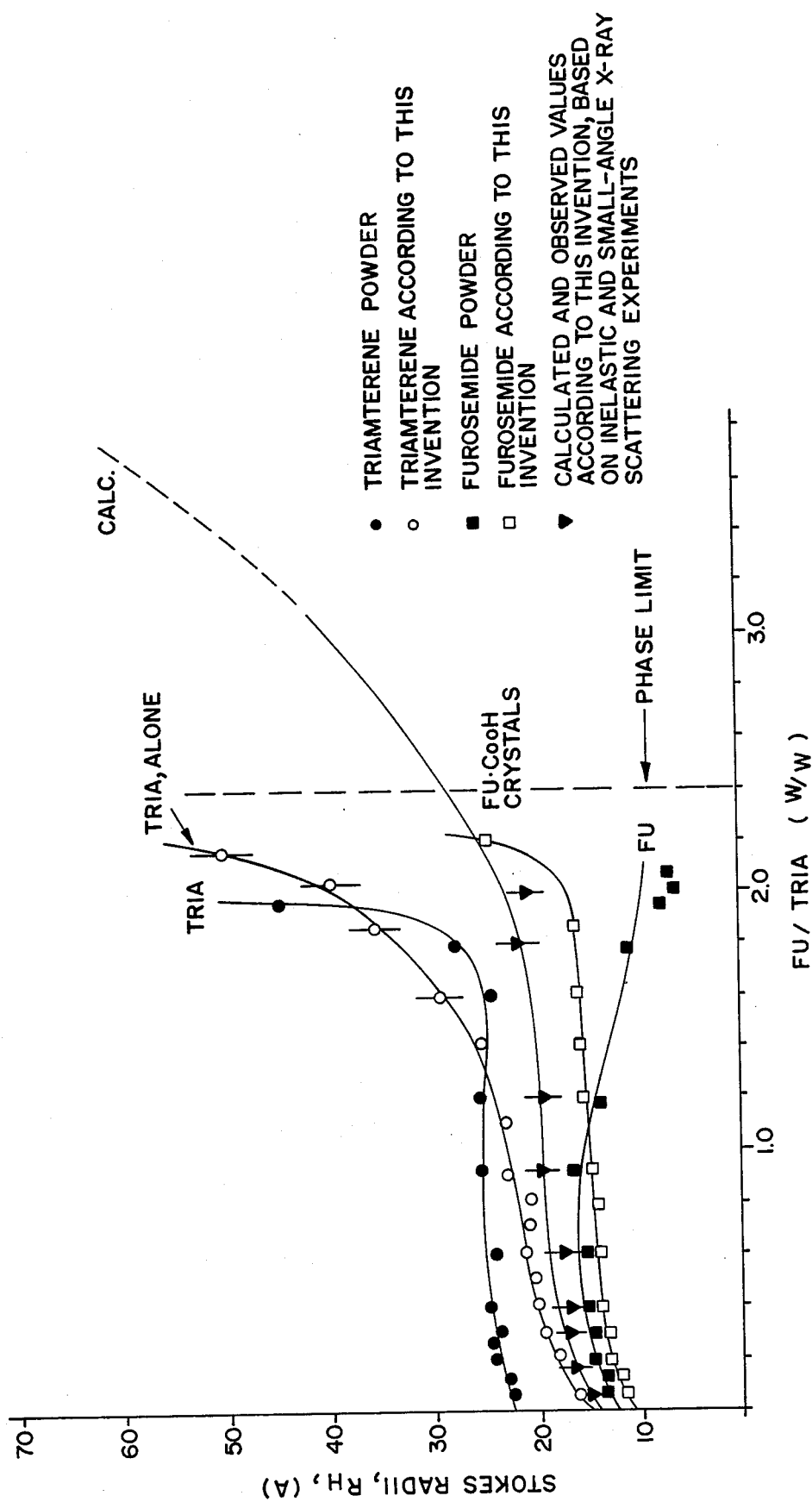

POTASSIUM-NEUTRAL SALURETICUM WITH ANTI-HYPERTENSIVE EFFECT

CROSS-REFERENCE TO RELATED APPLICATIONS

This application is a continuation-in-part of my co-pending application Ser. No. 773,812 filed Sept. 9, 1985, now abandoned which, in turn, is a continuation-in-part of application Ser. No. 522,037, filed Aug. 9, 1983, now abandoned.

FIELD OF THE INVENTION

This invention relates to a diuretically active composition of matter composed of triamterene and furosemide, the furosemide being in a controlled release form in order to facilitate solubilization thereof in triamterene micelles.

More particularly, the present invention is concerned with the preparation of a novel composition of matter composed of furosemide in controlled release form, and triamterene in a ratio of 1:2 (mol/mol) capable of forming mixed micelles in aqueous solutions between pH 1.5 to 9.5 thus providing a composition of low polydispersity and high stability.

BACKGROUND OF THE INVENTION

The advantages of administering orally active drugs in a sustained release form are numerous (see R. J. DeNeale and P. C. Guley, U.S. Pat. No. 4,248,857, Feb. 3, 1981; Remington's Pharmaceutical Science, 1980, Mack Publishing Co., Easton, PA 1590-1593).

It is also known, of course, that taking medication once a day instead of numerous times daily, especially for combinations such as diuretics with different pharmacodynamic actions eliminates a major source of inconvenience and insecurity for the patient as well as proving for a more even distribution of drug concentration in the blood. According to the pH-partition theory the absorbability of furosemide and triamterene, respectively, is favored when they are present in uncharged form at the absorption site and possess an intrinsic partition coefficient favoring a system like oil in an oil-water system. Since charged materials are oil-insoluble, those properties of drugs favoring their existence in fluids at absorption sites in the uncharged form favor their absorption. So furosemide as a weakly acidic drug will exist in the stomach in the undissociated form, and, therefore, its absorption will be favored from this pH-environment resulting in fairly quick action with considerable loss of potassium. Triamterene which is a weakly basic drug will exist at the same site as a protonated cation, hence charged and poorly absorbed which is consistent with in vivo experiments revealing a pharmocokinetic half life time of $t_{\frac{1}{2}}=3.0$ h versus $t_{\frac{1}{2}}=1.5$ h for furosemide in comparison.

Furosemide, peritanide, and bumetanide are advantageous in the treatment of edema and high blood pressure. They have a half life time of about 1 h versus 4 h in the case of the benzothiadiazides derivatives, for instance. The consequence of the very strong effect may be circulation problems which may even cause a collapse. Further undesirable pharmacological effects are inter alia an increase in uric acid, diabetogenous effects, influence on the metabolism, strong potassium losses and the massive stimulation of the plasma renin-angiotensin system.

From DE-AS No. 26 15 694 the combination of triamterene with cyclothiazide is known. When the individual dose is reduced, stronger total effects and fewer undesirable pharmaceutical side effects were observed also. However, the precondition for an ideal combination is the requisite that both active ingredients are almost identical in their pharmacokinetic half life time and supplement each other in their pharmacodynamics.

From Therapiewoche 30, 1980, pages 6831 to 6847 it is known that by the simultaneous intravenous administration of furosemide and hydroxy-triamterene-sulfuric acid ester, which attains a plasma concentration about ten times greater than triamterene, the potassium loss caused by furosemide can be impeded.

Celdran et al., (Arzneimittel-Forschung 1976, 26(11), 2073-2076) describe a preparation having diuretic activity consisting of 40 mg of furosemide Xanthinol and 25 mg triamterene which was given to patients separately.

Thompson et al., (Clin. Pharmacol. Ther., 1977, 21(4), 392-394) describe the effect upon administration of 40 mg/day of furosemide and 50 mg/day or 100 mg/day of triamterene. Both doses of triamterene are stated to augment the natriuretic effect. The dosage was determined empirically.

Stote et al., (J. Int. Med. Res., 1974, 2(6), 379-383), describe the oral dose of triamterene, 50 or 100 mg, required to block the kaliuretic effect of 40 mg furosemide in normal volunteers.

Azzi et al., (Clin. Ter., 1971, 56(6), 501-522) show the use of 80 mg of furosemide with 50 mg triamterene when administered to edema-bearing patients.

Lammintausta et al., studied the excretion and electrolyte excretion following administration of 80 mg furosemide and 100 mg of triamterene to healthy volunteers. (Lammintausta et al., Int. J. Clin. Pharmacol. Ther. Toxiol., 1980, 18(9), 395-398).

The patent ot Dahlhausen et al. No. 4,324,779 simply shows a slightly retarded formulation of furosemide including measurments and releases rates. As will be discussed later on with more particularity the method of Dahlhausen et al. will give false results when another diuretic is present in a combination of drugs with respect to dissolution rates and not simply release rates and physical state in solution.

The patent to Johnsen (U.S. Pat. No. 4,335,119, June 15, 1982) shows a pharmaceutical preparation of furosemide with the sulfate ester of 2,4,7-triamino-6-p-hydroxy-phenylpteridine and its physiologically permissible salts in a weight ratio of 1:10 to 5:1 (furosemide:pteridine component) with a preference of 1:4 to 2:1. Other researchers report chemical and pharmacodynamic results of various dosage forms of furosemide and triamterene administered separately manifesting the potassium loss through furosemide and its inhibition through triamterene (Azzi et al., Clin. Ter., 1971, 56(6), 501-522; Celdran et al., Arzneim.-Forschung 1976, 26(11), 2073-2076; Stote et al., J. Int. Med. Res., 1974, 2(6), 379-383; Lammintausta et al., Int. J. Clin. Pharmacol. Ther. Toxicol., 1980, 18(9), 395-398).

None of the foregoing references, showing various combinations in unrelated stoichiometry of furosemide and triamterene, teach the desirability of providing (i) a constant molar ration of furosemide to triamterene by an appropriate pharmaceutical formulation, yielding mixed micelles in aqueous solutions at pH 1.5 to pH 7.5, demonstrating that these mixed micelles are the physicochemical active pharmacons; (ii) nor do the references teach how to achieve these mixed micelles with high stability and low polydispersity in due time, e.g. indicating the very reduced concentrations of furosemide and triamterene-monomers in aqueous solutions; and (iii) the synergistic effect of reducing the dissolution rate of furosemide by triamterene through forming mixed micelles comprising binding furosemide onto triamterene micelles, quite unexpectedly at a constant ratio of furosemide to triamterene of 1.0:2.0.

It is, therefore, an object of the present invention to provide a novel pharmaceutical composition comprising furosemide, having a controlled release rate, and triamterene in a ratio of 1.0:2.0 (mol/mol) of low polydispersity and high stability.

It is a further object of the present invention to provide a new pharmaceutical combination of acidic and basic diuretically active ingredients with the formation of mixed micelles, induced through a controlled release form of furosemide which forms instantly mixed micelles in aqueous solutions with triamterene in a constant ratio of the former to the latter of 1.0:2.0.

These and other objects of the present invention are readily achieved by providing a potassium-neutral salureticum with anti-hypertensive effect by using a novel preparation of a combination of a controlled release form of furosemide and triamterene, having the following pharmacological properties at a constant ratio of 30 mg furosemide in controlled release form and 50 mg triamterene:
1. Rapid initial onset of the effect.
2. No abrupt and short effect, i.e. no rebound.
3. Maximally protracted effect lasting more than 10. h.
4. Good and simultaneously protective flooding out without circulation stress and without danger of thrombosis.
5. Effective even where the kidney function is restricted.
6. Potassium neutral, saving in magnesium and calcium ions.
7. As far as possible without influence on carbohydrate and fat metabolism as well as the separation of uric acid is concerned.
8. Less side effects, e.g. stomach disturbances due to triamterene.

BRIEF SUMMARY OF THE INVENTION

The present invention thus relates to a pharmaceutical composition forming mixed micelles in aqueous solutions between pH 1.5 to pH 9.5 of furosemide and triamterene having a ratio of 1.0:2.0 (mol/mol) of low polydispersity and high stability. In order to form this pharmaceutical composition in solution, furosemide has to be in a controlled release form by means of stearate, phthalate, etc., especially such inactive ingredients which are able to induce carboxyl-carboxylate or hydroxy-cyroxylate interactions, and in the case of furosemide and triamterene have to be coated as such to form mixed micelles of high stability, low polydispersity and constant aggregational numbers over pH 1.5 to pH 7.5, instantly. Preferably, the diuretically active agent furosemide should be in a form of controlled release in a molar ratio to triamterene of one to two, e.g., ~30 mg furosemide to ~50 mg triamterene where optimal saturation of triamterene micelles are obtained through furosemide, disclosing homogenity of this pharmaceutical formulation in aqueous solutions over a wide pH-range with constant aggregation numbers.

This pharmaceutical formulation of two diuretically active ingredients of constant ratio (w/w) favors the dissolution rate of furosemide in a synergistic way, e.g. depressing the release of monomers of furosemide into the aqueous phase by means of solubilization through triamterene. These unexpected phenomena are only achievable if the acidic ingredient of the diuretically active combination is in the form of a controlled release.

BRIEF DESCRIPTION OF THE DRAWINGS

Tables of Figures

FIGS. 7a, 7b, and 7c—Phase diagrams of the various combinations of furosemide/triamterene in aqueous solutions at 37° C.

FIG. 9—Dependence of the Stoke's radii of the various combinations of furosemide to triamterene, including the one according to this invention.

DETAILED DESCRIPTION OF THE INVENTION

Figure 1A:
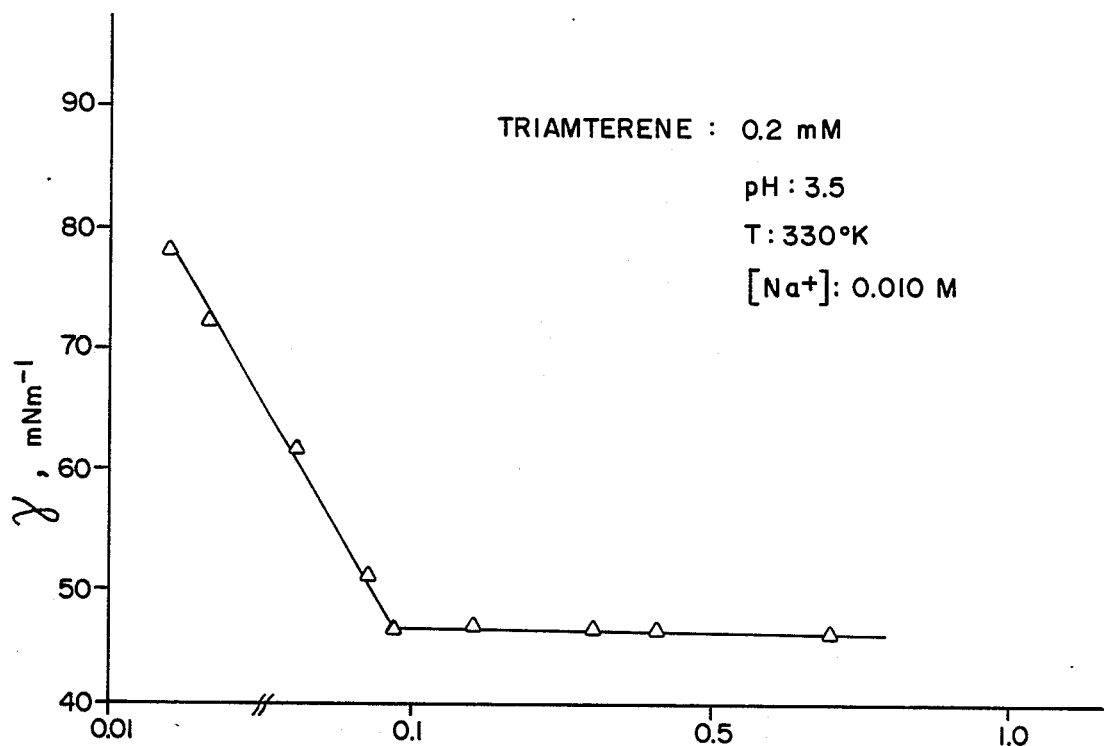
FIGS. 1A, B—Equilibrium Surface Tension measurements (A) in the presence of 0.2 mM Triamterene and (B) in the presence of 0.10 mM furosemide.

With respect to micellization, solubility and dissolution rate in vitro and in vivo, furosemide as well as triamterene have a very low solubility of 65 μm/ml (1.965 μM/l) and 30 μg/ml (1,184 μM/l) which is pH-dependent, however, more for furosemide than for triamterene. Both drugs do form micelles in aqueous solution between pH 1.15 and pH 9.0 micelles having critical micelle concentrations of $8.3 \times 10^{-5}$M furosemide (37° C.) and $1.5 \times 10^{-5}$M for triamterene (37° C.), respectively.

Furthermore, these two drugs dissimilar in structure which are surface active on forming micellar structure are able of generating liquid membranes in supporting coatings and supporting ingredients, so influencing not only the dissolution rates in vitro and in vivo, but also the amounts of each drug in a combination is of critical importance since they do influence on a physical-chemical basis each other with the result of forming insoluble materials, e.g. coercervates along a consolidation curve, as seen by the production of triamterene stones in the kidneys by combination of thiazide-diuretics with triamterene (F. Sorgel et al., J. Pharm. Sci. 75, 129, 1986, and citations therein) decreasing or increasing the solubility of each component in an unrelated combination on molar basis with the result of precipitation in the stomach and kidneys with its side effects, or by impeding of ions in an uncontrolled manner by unknown actions of increased solubility of one of the components within the combination. Furthermore, in the case of hydrophobic materials, e.g. furosemide and triamterene, it is important to know if their micelles fuse together in the pharmaceutical formulations yielding a mixed micelle, or whether they form separate micelles with a very high degree of variation in size, molecular weight and aggregational number, so that a certain amount of monomers below the CMC remains in solution with a high degree of variation ($<n_w>$, $<n_n>$). Since the pharmaceutical preparations, including the various dosage forms and sustained release forms, of these two drugs in general well above the CMC, the remaining questions are of importance especially for hydrophobic substances, to draw conclusions about the in vitro in vivo release by means of dissolution techniques as describeb by Dahlhausen et al. (U.S. Pat. No. 4,325,779), since they do not consider e.g. the equilibrium between monomer and micelles, the equilibrium between the forming of mixed micelles by combinations, the equilibrium between dissociated and un-dissociated forms which is preserved by formation of more undissociated (protonated) acid from protonated forms of triamterene, as the former materials leave the absorption site. Furthermore, a considerable drawback of the flow cell system according to Dahlhausen et al., is the inability of determining the sequence of events in the dissolution rates of two active substances, e.g. furosemide and triamterene, separately and their influence on each other. This is also true for micellar system, since inelastic light scattering methods have to be applied to correlate kinetic dissolution rates and micellar growth or micellar catalysis.

Measurements of the contact angles of triamterene and furosemide reveal values of 100 deg. and 59 deg. respectively, indicating a strong hydrophobic nature in case of triamterene, resulting in wetting problems, whereas furosemide is only slightly hydrophobic. However, this determined hydrophobicity can be changed drastically by effecting the crystallographic structure due to complexing to stearate, phthalate, etc., resulting in a contact angle of furosemide to 108 deg. This makes it possible that both substances with their similar contact angles reduce the wetting problems and increase the spreading of furosemide in the presence of triamterene by forming mixed micelles of constant size and polydispersity. Moreover, the CMC for both substances are now in the range of $1.5\times 10^{-4}M$-$2.5\times 10^{-4}M$ determined by surface tension measurements. (See FIG. 1)

Figure 1B:
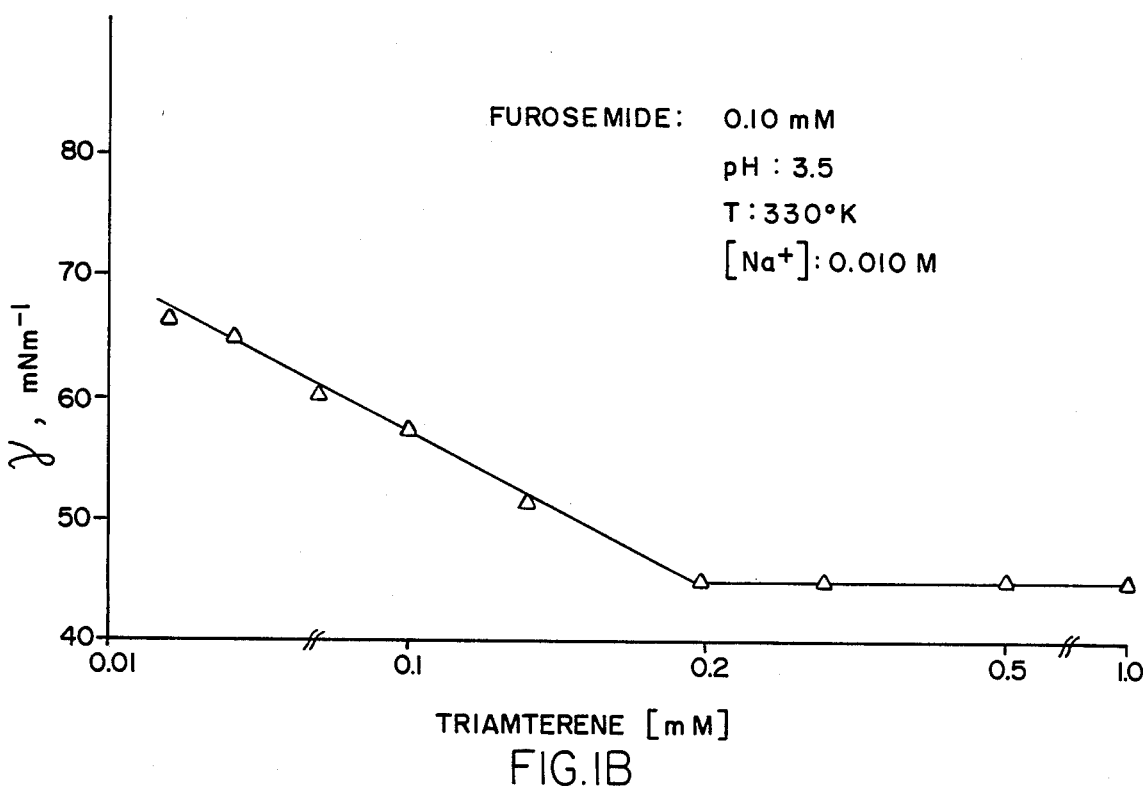

FIGS. 1A, B show the equilibrium surface tension measurements according to this invention applying a controlled release form of furosemide and triamterene. However, in addition, various different ratios of furosemide and triamterene are also shown. In FIG. 1A the concentration of triamterene was kept constant, in the other one the concentration of furosemide was kept constant (FIG. 1B). Each set of data can well be fitted to a straight line, which intersects furosemide or triamterene concentration which is normally taken as the CMC. Note the sharp break points in both graphical representations are not the same or identical with those of the CMC's of triamterene or furosemide, respectively. Quite unexpected is the sharp drop to a surface tension of $\sim 45$ mNm$^{-1}$ at concentration of furosemide of 0.1 mM and 0.2 mM of triamterene, verifying that this molar ratio is apparently optimal in its solution composition, since higher ratios have no influence of the surface activities whatsoever. The differences between the CMC of the substances furosemide and triamterene separately of $8.3\times 10^{-5}M$ for furosemide and $1.5\times 10^{-5}M$ for triamterene and the new one of $1.5$-$2.5\times 10^{-4}M$ support the proposition that the pharmaceutical composition of this invention has to be in the molar ratio of 1:2 (w/w) for furosemide and triamterene. This is further supported by measuring the pressure ($\pi$)-molecular are (Å$^2$) isotherm for furosemide, triamterene separately as well as for the combination according to this invention. Since the interfacial molecular areas can be determined from the slopes of equilibrium surface tensions measurements from FIG. A,B, just below the break points, they are easy to compare. As the result the isotherms indicate that the mixed micelles can form coherent films at $\sim 210$ Å$^2$/molecule (furosemide/triamterene) and have very similar states when $\zeta$ is $\sim 25$ mNm$^{-1}$. Hence except for triamterene and furosemide separately, the pharmaceutical composition according to this invention forms surface monolayers areas, and confirming other hydrodynamic results including small-angle x-ray scattering experiments, that these mixed micelles according to this invention lie almost flat at interfaces with the polar groups (carboxyl groups of furosemide, e.g.) projecting into the aqueous phase, and the hydrophobic molecule of triamterene disappears from the aqueous phase. Moreover, furosemide as well as triamterene are surface active and particularly furosemide binds to amphiphilic surface with the highest molar ratio of furosemide to triamterene of 1:2. As can be shown by monolayer studies of furosemide at alkaline pH, furosemide as part of the protonated species forms stable insoluble monolayers, indicating that deprotonation increases surface stability. The increase in surface stability which accompanies deprotonation is also reflected by a concomitant increase in the affinity of the uncharged compound towards an amphiphilic surface, as it is triamterene.

One important and quite unexpected result is the finding that furosemide—which is highly unstable in acidic solution due to proton-catalyzed hydrolysis in a pseudo-first order reaction—is now highly stable in acidic solution due to forming of stable mixed micelles of constant size.

Figure 2:
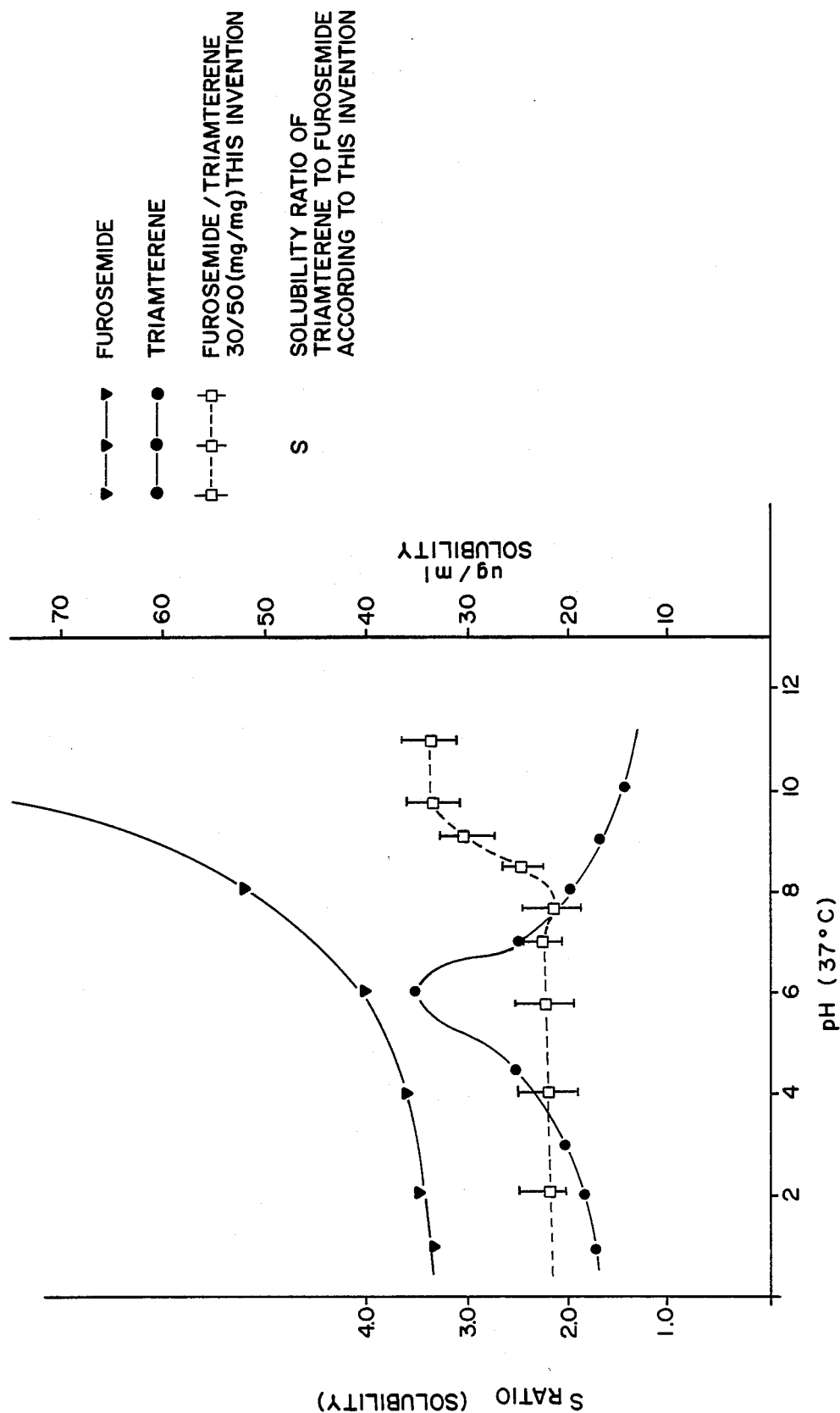
FIG. 2—Ratio (S) of solubility of triamterene to furosemide versus pH.

The solubility of furosemide at 37° C. is 35 mg/l equivalent to $0.1965\times 10^{-3}$ Mol/l (0.19 mMol), whereas the solubility of triamterene is determined to be 30 mg/l, equivalent $0.1184\times 10^{-3}$ Mol/l (0,11 mMol), resulting in a ratio of furosemide to triamterene of approximately 1.73 on a molar ratio or 2.16 on absolute gram ratio. Both ratios, for furosemide as well as for triamterene, are well above the CMC. Since triamterene in solution is forming dimers mainly at low concentrations below the CMC in aqueous solution as determined by inelastic high scatteriang experiments, single crystal structure determination, as well as small-angle x-ray scattering experiments, show the absolute ratio of furosemide to triamterene will be 0.5 to 1.0 at 37° C. This quite unexpected result reveals the optimum ratio of the solubilities of furosemide and triamterene between pH 1.5-7.0; at 7.0, whereas the solubilities of furosemide and triamterene are themselves pH-dependent; whereas the solubility of furosemide increases with pH due to formation of an anion and carboxylate carboxy-interactions, respectively, the solubility of triamterene decreases with pH rapidly from 30 mg/liter at pH 5.5 to 5 mg/liter at pH 9–11.0. However, the ratio increases in a sigmoidal mode to a constant of 3.25 (FIG. 2). This solubility behavior is only observable at the constant ratio of furosemide to triamterene. However, deviations from this constant ratio of furosemide to triamterene, e.g. a ratio of 40 mg furosemide to 25 mg triamterene or 80 mg furosemide to 100 mg triamterene exhibits in maxima or minima of the solubility curves because, in the first case, triamterene is solubilized in furosemide, and in the second case, the solubilization of furosemide in triamterene by decreasing the solubility of triamterene whereas in the first case the solubility of furosemide is being increased (FIG. 2).

Comparison of the effects of triamterene in aqueous solution, even in the presence of salt, on the dissolution rate and solubility of furosemide suggest that triamterene increases the solution rate of furosemide at high pH, decreasing the solution rate of furosemide at low pH. This is furthermore an indication of micellar solubilization spreading in the first case and wetting effects in the second case when furosemide is not in controlled release form.

DISSOLUTION RATES OF THE INVENTION

The release profiles of the combination according to this invention, side-by-side to other ratios of furosemide to triamterene, where furosemide is slightly released reveal that at a ratio of 1:2 the release profile consists of only one component: the mixed micelles, consisting of triamterene and furosemide. Slight increases in permeation of this "solute" from slightly sustained furosemide and coated triamterene (ratio 1:2) from suspension between pH 1.5 to 5.5 are caused by stearate, phthalate (0.5%) because of wetting effects and promotion of dissolution of the "solute". Such effects require the solutions to be saturated which is the case in the composition of the invention having a ratio of furosemide to triamterene of 1:2 (FIG. 3).

The other release profiles of the plain sustances without sonifying do show the release of the drug separately, reflecting their different micellar hydrophobicity and spreading as determined by contact angle measurements also.

Furthermore, calculation of the concentration of furosemide of this invented combination in the aqueous phase at pH 1.5 to 3.5 according to the equation (1) when the total concentration of furosemide is known with C=concentration, with a=aqueous and m=micellar phase (triamterene)
V=volume; P=partition coefficient
t=sum of aqueous and miscellar phase
superscript $^o$ and $^-$ denote unionized and ionized furosemide
$f_i$=fraction of furosemide ionized at any pH it was found that only 0.5–1.0% free furosemide was in solution, whereas 99.0–99.5% (w/w) of furosemide was found in the triamterene fraction. If only aqueous furosemide was available for absorption after release, and provided that triamterene did not influence release by mechanism other than solubilization, an average of 1.8% at pH 1.5 or 2.5% at pH 3.5, of 30 mg/50 mg furosemide/triamterene per ml solution should be found in aqueous solution after 30 to 60 min. respectively. These figures are considerably higher than the corresponding experimentally determined ones in vitro, on the order of 8%, than those actually found.

Figure 3A:
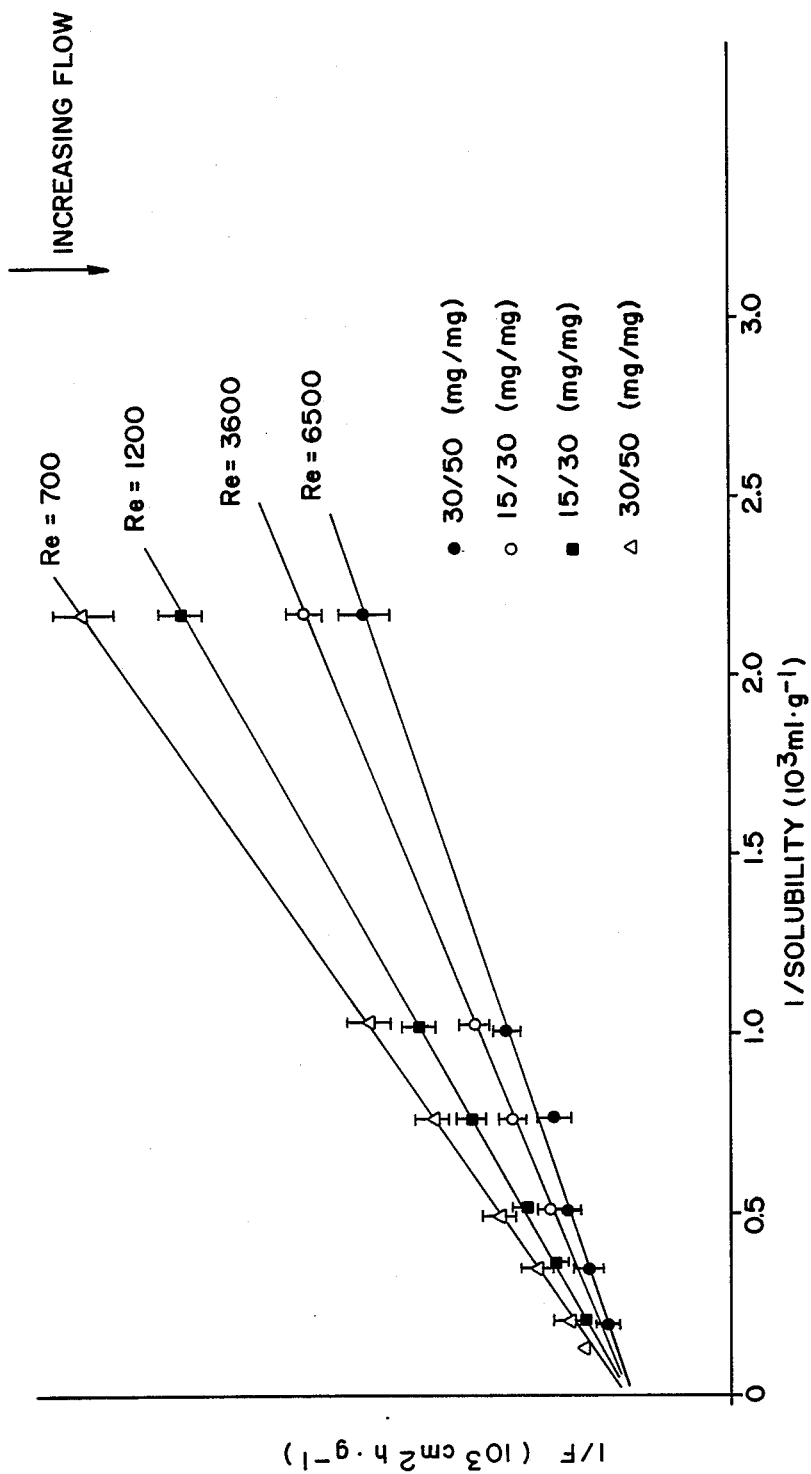
FIGS. 3—(A) Dissolution rates of furosemide according to this invention in the presence of triamterene at pH3.5—very similar between pH 1.5 to 5.5—the dependence of the agitation velocity (B) Model, showing the rate processes.
Figure 3B:
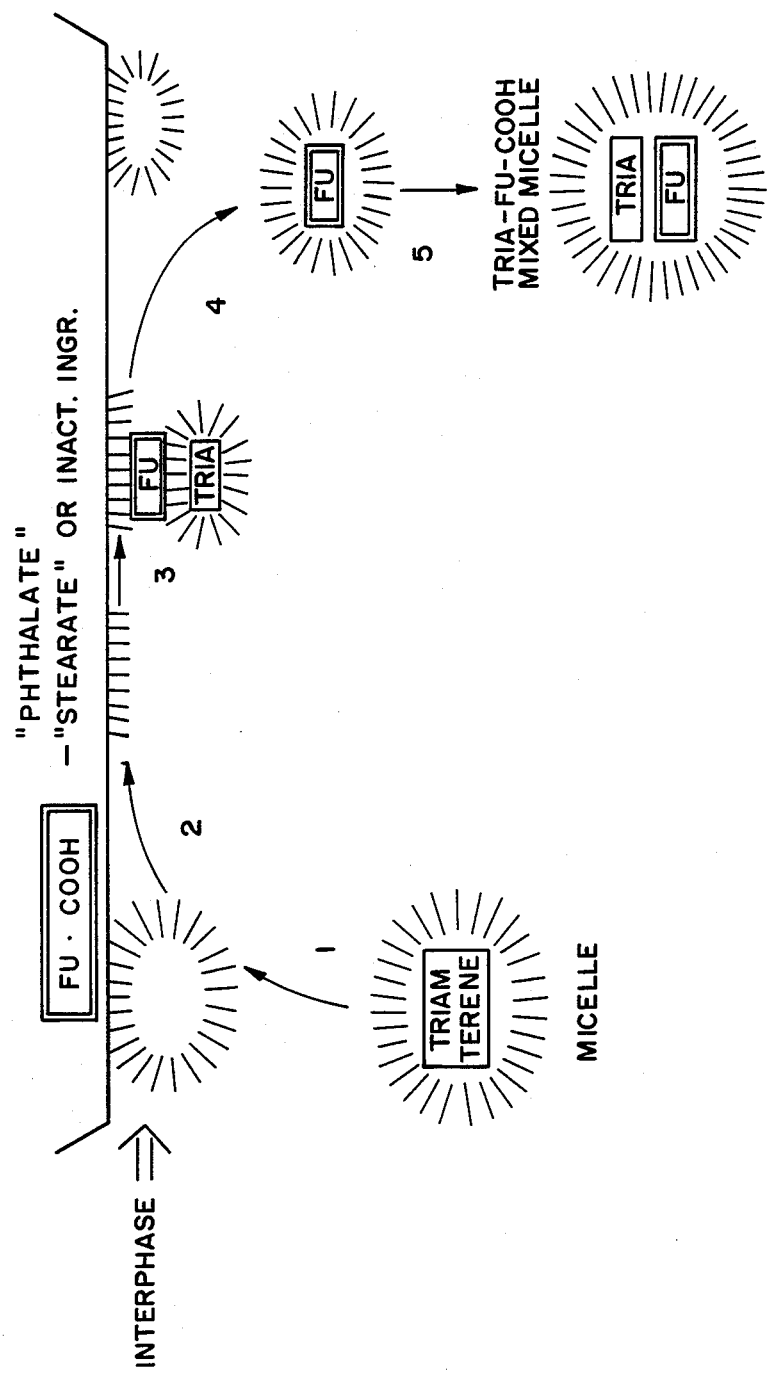
Figure 4:
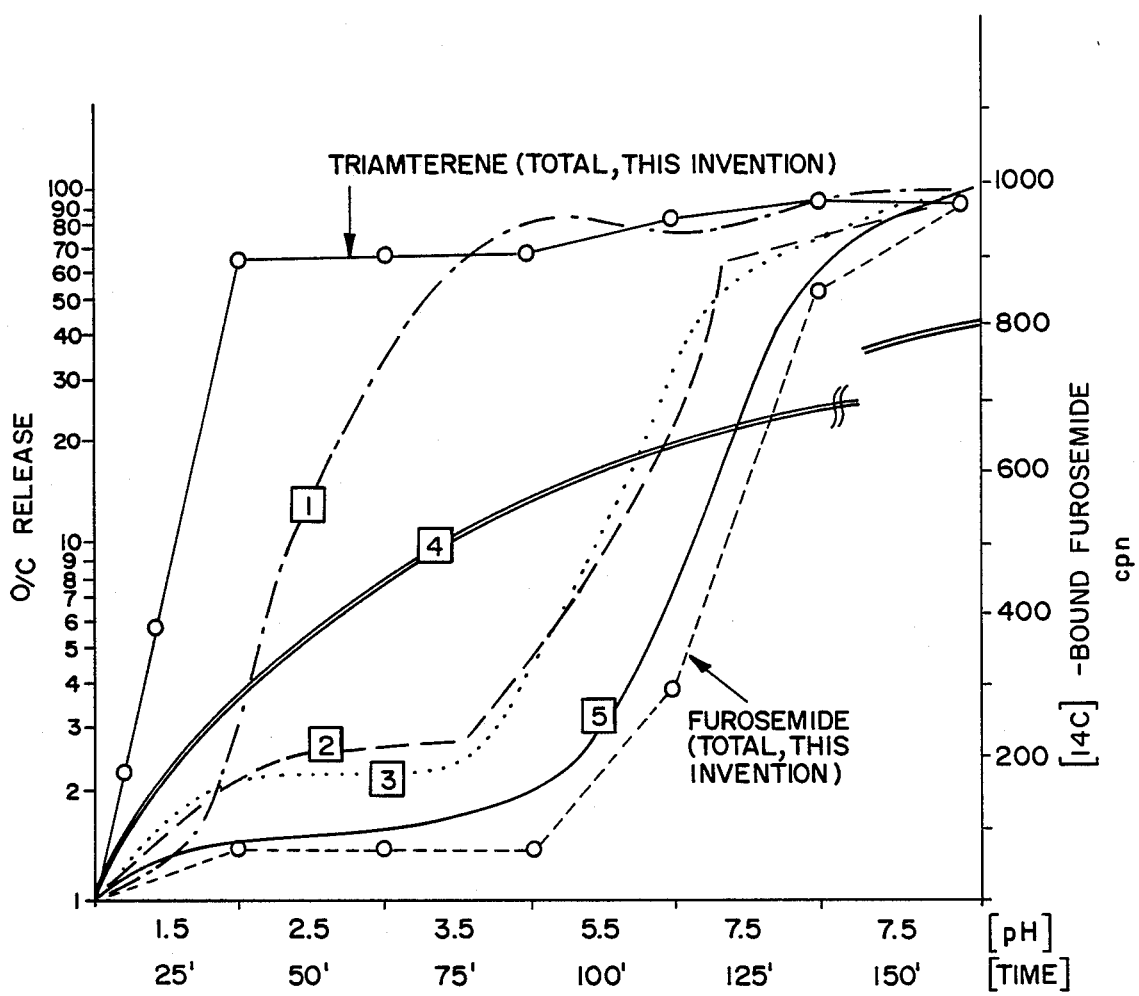
FIG. 4—Dissolution rates (%) release of furosemide vs. pH; (37° C.) and binding of furosemide to triamterene according to this invention.

The dissolution and kinetics of the dissolution of furosemide at various pH's according to FIGS. 3, 4, obey the Hixson-Crowell cube root ($W_o^{\frac{1}{3}} - W^{\frac{1}{3}} = K_{diss} \cdot t$), showing a biphasic pattern. The initial slope gives way to a second lower slope after time intervals of 30 to 60 min. However, the relation between dissolution rate and flow rate, e.g. agitation intensity—which has not been considered by Dahlhausen et al. especially of micellar solutions—is of upmost importance of forming mixed micelles of low polydispersity. If dissolution or solubilization of furosemide in micellar solutions of triamterene is diffusion controlled only, n=1 in the equation (V. G. Levich, "Physicochemical Hydrodynamics", Prentice-Hall, N.Y., (1962)

$$\log k = n \cdot \log v + \log f D,$$

with k the instrinic dissolution rate constant D, is the diffusion coefficient, $v$ is the flow rate and agitation velocities but, for interfacially controlled reactions, the reaction rate is independent of agitation intensity and n equals almost zero, which is the case according to this invention, but not so as described by Dahlhausen et al. or loose combinations of furosemide and triamterene at various unrelated molar ratios. Since the variation in stirring rate-reaction rate relationship is also due to variations in solvent turbulence near the interface, n is of the order of 0.35–0.5 for laminar flow and n~0.8–0.9 for turbulent flow.

Figure 5:
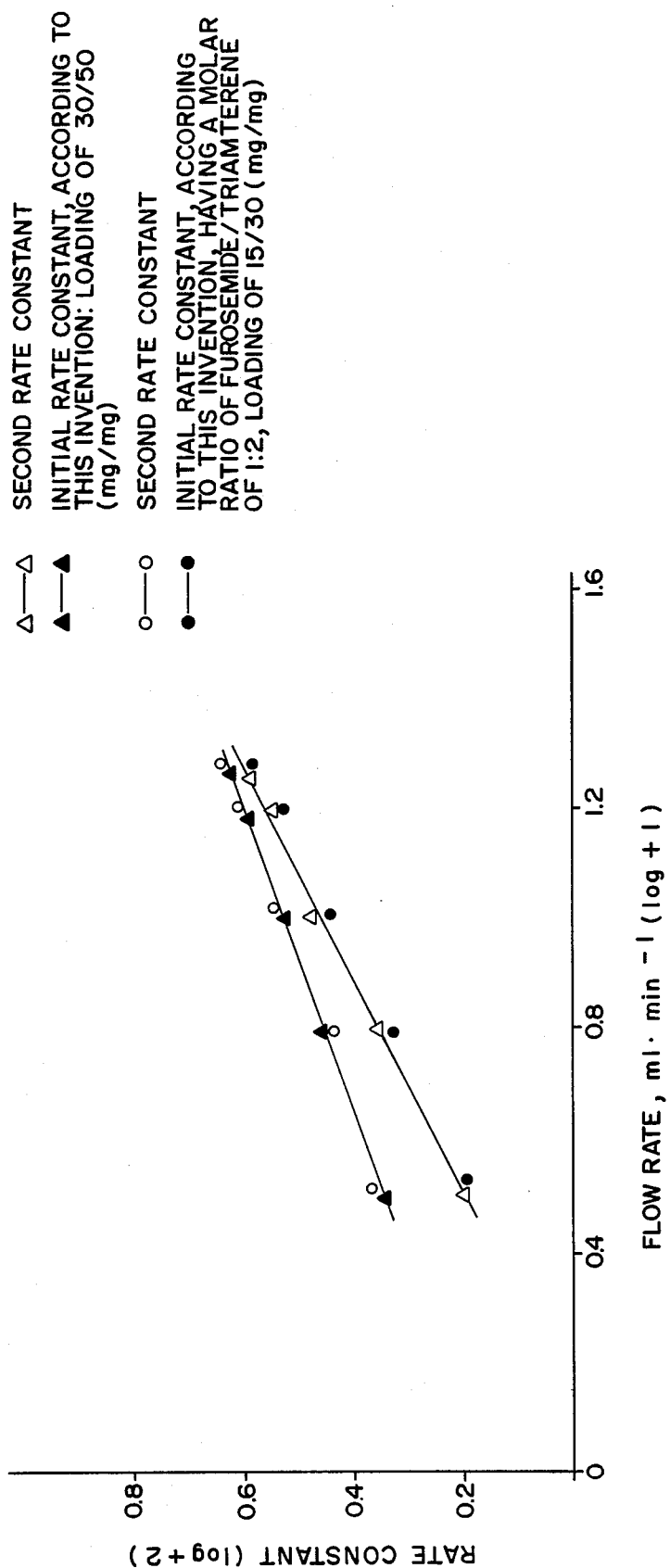
FIG. 5—Dissolution rates and kinetics for furosemide in determining the reaction rates and kinetic constants (initial and second rate constants) of release of furosemide according to this invention.
Figure 6A:
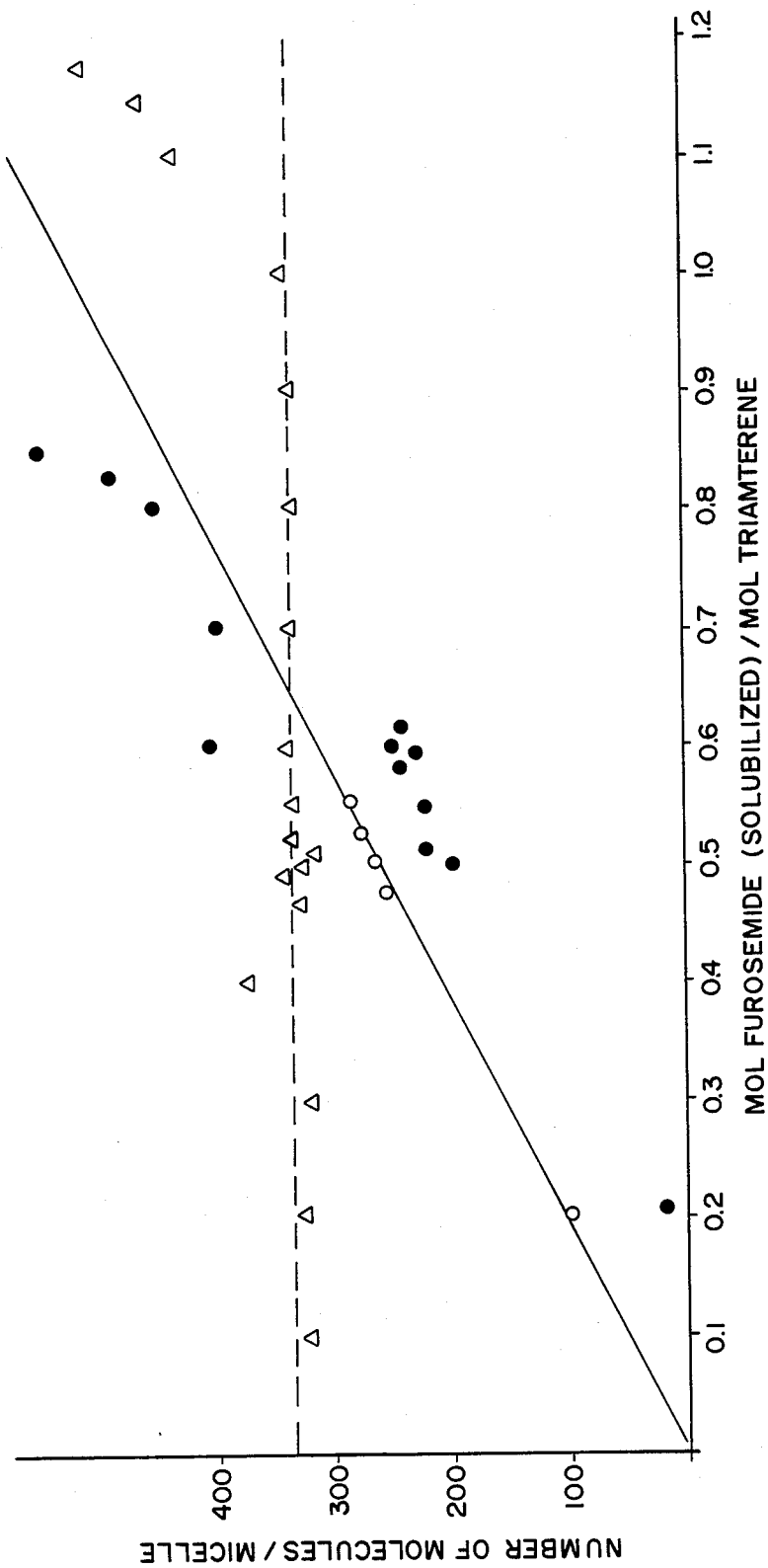
FIGS. 6—(A) number of molecular furosemide bound to triamterene micelles according to this invention. (B) when using the procedure of Dahlhausen et al., only.
Figure 6B:
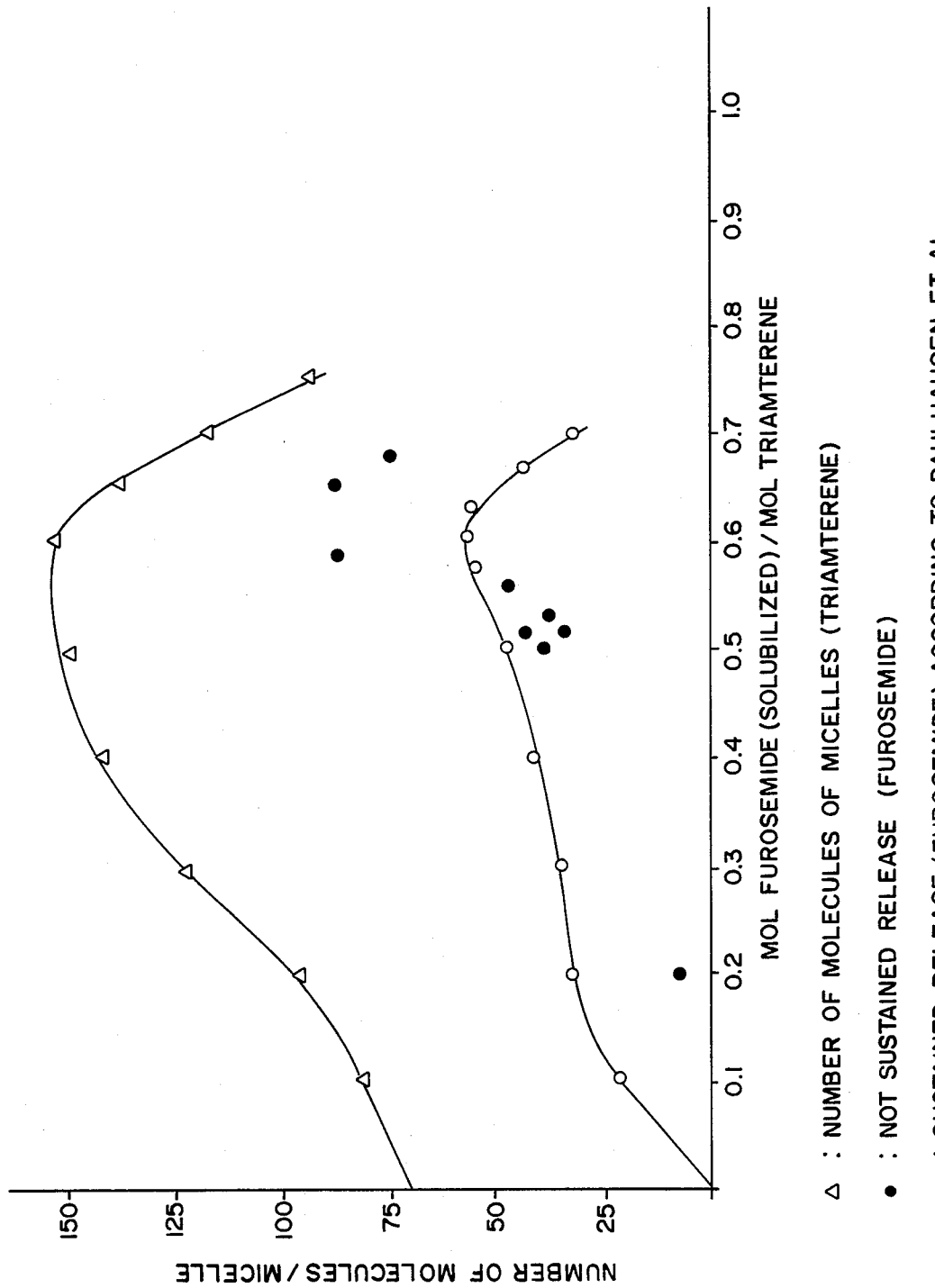

In the present invention n is determined from the initial and second rate constants of 0.27 and 0.37, respectively, FIG. 5, whereas for loose combinations values of 0.85 are determined, indicating turbulent flow and release of furosemide in diffusion controlled way. The release of furosemide from pharmaceutical formulations according to Dahlhausen et al. is diffusion controlled and turbulent in flow (n~0.89). This preparation is not suitable for the aim of this invention, since, in addition to having a saturated molar ratio of two (furosemide to triamterene) in a homogeneous solution, laminar flow is needed to form mixed micelles at the interface of low polydispersity in size and aggregational numbers. This $$C_a = C_t \frac{V_t}{(P^o V_m/V_a) + P^- V_m/[(1/f_i) - 1] V_a + 1 + 1/V_a [(1/f_i) - 2]} \times \left[ 1 + \frac{1}{(f_i/f_i) - 1} \right] \quad (1)$$

is supported by the FIGS. 3 and 4, as well as by determining the Stokes radii by inelastic light-and small-angle x-ray scattering, surface-tension measurements and binding experiments as shown in FIGS. 6A, B. FIG. 6B shows the difference of the invented controlled release preparation according to Dahlhausen et al., revealing a completely different solubilization of furosemide in the presence of triamterene.

The slower dissolution rate of furosemide, when in a controlled release form, and in the presence of molar amounts of triamterene is attributable to the nature of the interaction of the interface of furosemide—stearate (phthalate) and triamterene, which has a higher density and a lower porosity than the e.g. compressed particles in loose combinations. This view is supported by the scanning electron micrographs and diffuse (small)-angle x-ray scattering measurements also. Moreover, since powders, or formulations of furosemide differ from those described in this invention, have a higher porosity, and show a linear slope of the dissolution curve, while the preparation according to this invention shows a biphasic behavior, expressing the interactions with triamterene as well, is further supported by the kinetic follow up of the pharmacokinetic behavior in the blood for both substances.

Due to the interactions of furosemide with the inactive ingredients, e.g. stearate and phthalate including the interactions of the micellar solution of triamterene with the surface in which furosemide is being embedded, the eutectic melt (furosemide in this controlled release formulation) in the presence of triamterene has a slower dissolution rate as that compared to Dahlhausen et al. Since furosemide according to this invention is dispersed at the interphase in triamterene at the molecular level, furosemide molecules diffuse through a continuous phase of triamterene, which results in a much slower rate than is achieved when furosemide is being released as described by Dahlhausen et al. or in a normal pharmaceutical way, when furosemide is leached out through channels created when furosemide dissolves in the permeating dissolution solvent. The formation of liquid membranes of both drugs according to this invention supports this view.

The phase-diagrams of the various pharmaceutical formulations including the phase diagram according to this invention, are shown in FIGS. 7(A, B, C).

In general, the small-rod shaped micelles of triamterene at pH 3.0–5.0, as well as at pH 1.5 can solubilize certain quantities of furosemide. However, they reach a point (M) where they disintegrate, and form a molecular dispersion which, in turn, results in a loss of mutual solubility. FIG. 7B reveals that all the drawbacks according to FIGS. 7A, C are avoided when preparing furosemide in controlled release form and triamterene having a ratio of furosemide to triamterene of 1:1 or 1:2. Higher ratios as 1:2 or 2:1 are unfavorable since after having formed the 1:1 or 1:2 mixed micelles consisting of furosemide and triamterene, the excess will induce phase separation, liquid crystals and not an isotropic liquid solution anymore. It will yield a diagram like FIG. 7C.

Association and dissociation rate constants for the invented combination of furosemide to triamterene having a molar ratio of 1:2 (37° C.), are shown in Table 1 below. The data in the table are obtained from kinetic experiments using triamterene micelles ("liquid membranes") equal amounts as used in this invention. The ratio-ligand was $C^{14}$-furosemide at a concentration of 0.35 μM from a controlled release form according to this invention. The first two columns are the experimental data, i.e. time and specific binding at pH 3.5 and 37° C. The value for $B_e$ (found concentration at equilibrium) was taken as 700 cpm. The amount of non-specific binding was 800 cpm, and did not change as a function of time. (Table 1).

Figure 8A:
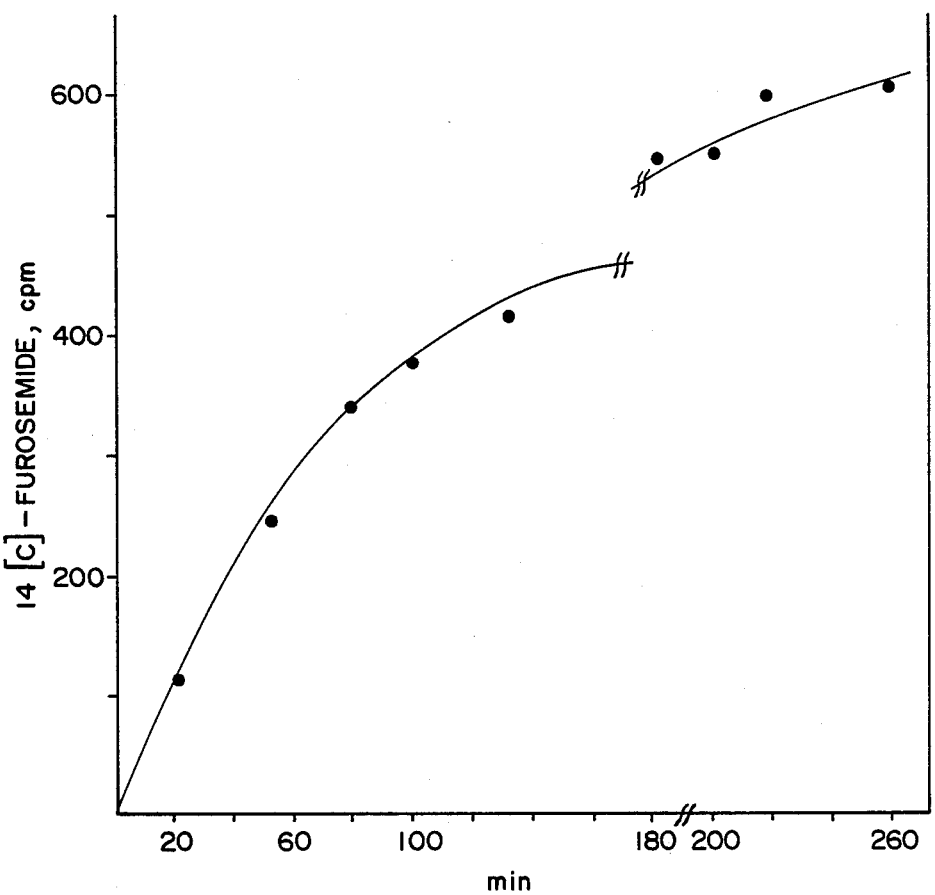
FIGS. 8A, B shows binding experiments according to Table 1.
Figure 8B:
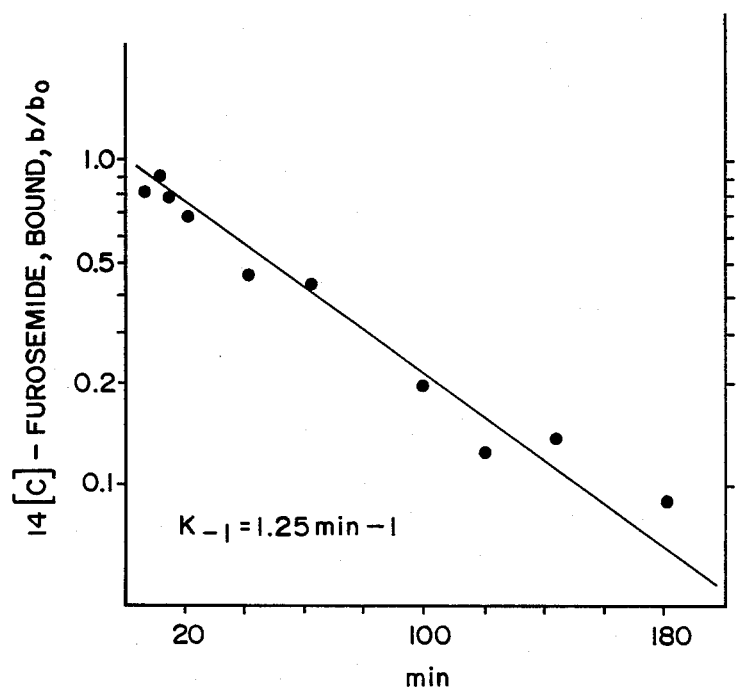

The data obtained for these binding experiments are plotted in FIGS. 8(A, B). It must be emphasized that if the reaction is not simply a bimolecular one, a non-linear plot may result. This is the case if one does the same experiments with concentrations of furosemide and triamterene, in loose combinations and unrelated molar ratios.

TABLE 1

| Data for Association and Dissociation rate constants for furosemide in a controlled release form and triamterene (1:2) | | | |
|---|---|---|---|
| Time min. | B | Be/Be—B | Be en Be—B |
| 0.0 | 0 | 1.00 | 0.00 |
| 15.0 | 130 | 1.25 | 0.15 |
| 25.0 | 300 | 1.67 | 0.45 |
| 40.0 | 321 | 1.55 | 0.49 |
| 60.0 | 475 | 2.94 | 1.05 |
| 80.0 | 560 | 5.00 | 1.70 |
| 100.0 | 620 | 6.71 | 1.89 |
| 130.0 | 635 | 11.00 | 2.50 |
| 160.0 | 750 | | |

$k_{obs}$ was evaluated to be 1.0 min$^{-1}$, using the $k_{-1}$ value of 1.25 obtained for the dissociation rate, $k_{+1} = (k_{obs} - k_{-1})/\text{Tria} = (1.9 - 1.25)/0.35 = 1.857$ min$^{-1}$ μMol$^{-1}$.

From the estimate of $k_{+1}$ and $k_{-1}$, $K_D$, the dissociation constant of this combination at a molar ratio of 1:2 (furosemide to triamterene), can be calculated:

$$K_D = \frac{k_{-1}}{k_{+1}} = \frac{1,900}{1,857} = 1,02 \ \mu\text{Mol}$$

This value is in good agreement with $K_D$ of 1.05+/−0.05 μMol determined from saturation experiments. These results clearly show that triamterene, which is well above the CMC when the dissolution rates are determined in combination with furosemide, increased the partitioning of the furosemide, when in controlled release form, into the micellar phase of triamterene by binding between triamterene and furosemide forming a more liquid solute species.

The effect on the micelle size of triamterene of solubilization of furosemide at different ratios is shown in FIGS. 6A and 9. It can be concluded that no increase of molecule weight of the triamterene micelles due to an increase in both the number of solubilized furosemide and triamterene molecules per micellar unit, indicating no location of furosemide in the inner core of the triamterene micelles. This is supported by measurements of the hydrodynamic radii through inelastic light scattering and small-angle x-ray scattering experiments as shown in FIG. 9, and listed in Table II—The polydispersity of the mixed micellar solutions was evaluated as follows: a polydisperse system has to be considered where each micellar component 1 is specified by its molecular weight $M_1$, radius of gyration $R_{g1}$, diffusion coefficient $D_1$, form factor for light or x-ray scattering $P_1$ and concentration $C_1$. The fraction $G_1$ of the total light intensity scattered by component 1 is given through equation:

$$G_1 = \frac{C_1 \, M_1 \, P_1}{\Sigma C_1 \, M_1 \, P_1}$$

The analysis of cumulants of the autocorrelation function of the scattered light intensity provides statistical measures of the distribution of diffusion coefficients, $D_1$, where each component is weighed by $G_1$. The mean value of $\overline{D}$ or $\overline{R}_g$ is given by $$\overline{D} = \Sigma \, G_1 \cdot D_1 = \frac{k_B \cdot T}{6\pi\eta_o \cdot \overline{R}_H}$$

The variance V is related to the second moment of the distribution, $\overline{D}^2$, as:

$$\overline{D}^2 = \Sigma G_i D_i^2$$

and $$V = 100(\overline{D^2} - \overline{D}^2)^{\frac{1}{2}}/\overline{D}(\%)$$

listed in Table II "V" is of the order of 9-11% according to this invention, loose combination of furosemide and triamterene of the oder of 45-55%.

However, a slight decrease in molecular weight was detected by membrane and vapor pressure osmometry at furosemide concentrations having a ratio of furosemide to triamterene of 05:1.0 which is the saturation concentration for furosemide. The solubilization of furosemide involves possibly the hydrophobic region of triamterene-micelles whereas the number of triamterene molecules per micelle remains constant. (FIG. 6A)

The solubilization kinetics of furosemide in this particular combination is shown in FIG. 4. These data support the findings that mixed micelle desorption and diffusion are rate controlling in the presence of triamterene having the optimum ratio of furosemide/triamterene 0.5 to 1.0. Substantial effects on the dissolution rate is evident at this particular combination in this molar ratio when furosemide concentration in solution approaches saturation solubility, since an equilibrium exists between the solid of the controlled release form of furosemide and the micellar triamterene solution at the interface and the rate is controlled by the diffusion of free and solubilized solute across the diffusion layer of a certain thickness made by the formulation of the controlled release form of furosemide.

$$\overline{S} = n\left[\frac{1 + K(T) S_o(T)}{K(T) S_o(T)}\right]$$

with $\overline{n}$ = the aggregation number of triamterene miscelles, $K(T)$ the furosemide binding constant, $S_o(T)$ the monomeric solubility of furosemide which is temperature dependent, if $K(T) S_o(T)$ is $>>1$, S does approach the limiting value of $\overline{n}$, which is 15 and 25, respectively, at pH 2.5 and 7.9. Conversely, if $K(T) S_o(T)$ is $<<1$, S will be $>>n_o$ as is the case of the claimed combination having a maximum of 33.0-35.0 mg. Using the experimental values of n and S (Table 1) and the value for the solubility of furosemide in water at 37° C. $(1.965 \times 10^{-6} M)$ a value of K (37° C.) equals to $5.0 \times 10^6$ l/mol, and at 20° C. K (20° C.) equals to $4.8 \times 10^6$ l/mol. Since the K(T) value for the triamterene miscelle is roughly 15 times smaller than for a furosemide micelle, it is easily to be seen why the former micelles are superior solubilizers of furosemide than furosemide micelles for triamterene, even when furosemide is in the charged state. The standard energy change associated with the solubilization of furosemide in the triamterene micelles correspond to 12.7 Kcal/mol at 20° C., thus the binding of furosemide to the triamterene miscelles is more favorable by $\infty 5$ Kcal/mol than binding of triamterene to the small furosemide micelles which are very unstable in solution. The fact, that the $\Delta G$ values differ markedly between these two micelles suggests that furosemide binding to the triamterene micelles must have a strong interaction with the micellar triamterene surfaces, especially having a maximum at a ratio of furosemide to triamterene of 0.5:1, rather

TABLE II

Micellar and Molecular Properties of furosemide and triamterene according to this invention.

| No. | CMC | Solubility (mM) of furosemide as a function of triamterene | $P_{Ka}$ 37° C. | Molecular Area $(A^2)^e$ | $\overline{R}_H^f$ (A) | $\overline{n}^g$ | $V_{(\%)}$ |
|---|---|---|---|---|---|---|---|
| $1^a$ | $1,5 \times 10^{-4}$ $2,5 \times 10^{-4}$ | $0,105 (1:2)^d$ | 5,97 | 88 (85) | $20,5 \pm 1,5$ | 15 | 9 |
| $2^b$ | $1,9 \times 10^{-4}$ | $0,0955 (1:2)^d$ | 5,95 | 100 (95) | $25,1 \pm 1,5$ | 22 | 10 |
| $3^c$ | $2,2 \times 10^{-4}$ | $0,110 (1:2)^d$ | 6,00 | 95 (90) | $23,5 \pm 1,5$ | 20 | 10 |

$^a$determined by surface tension measurements,
$^b$by light scattering experiments,
$^c$fluorescense titration;
$^d$furosemide to triamterene molar ratio at saturation,
$^e$by surface tension at pH 7,2; values in parenthesis are derived from the slope of the equilibrium surface tension measurements and from the monolayer collapse point of the $\pi$-A isotherms.
$^f R_H$ at CMC; $\overline{n}$: aggregational numbers, rounded off, as determined by inelastic light scattering measurements.
$^g$variances; determined through inelastic light scattering.

FUROSEMIDE SOLUBILIZATION RELATED TO CONTROLLED RELEASE

Since the mean hydrodynamic radii of triamterene and salt-triamterene at various pH's micelles change only slightly when furosemide in one of the described preparations in the example section which follows is solubilized, these results suggest that the incorporation of furosemide molecules into triamterene miscelles does not markedly alter their preexisting structure, since this would have been evident because they would have made the dominant contribution to the measured $\overline{R}_H$-radii (FIG. 9). Assuming a single furosemide molecule binding site characterized by a temperature-dependent binding constant K(T), the ratio of triamterene to furosemide molecules corresponding to the maximum degree of solubilization, S, according to the equation than with the micelles interior of triamterene. However, due to the micellar size, dissolution behavior, as well as the solubilizing capacity $(S^{-1})$ of triamterene for furosemide, it can be concluded on thermodynamic grounds, measurements of the contact angles and surface tensions, that roughly half of the triamterene surface will be eliminated from water contact $(\sim 37 \text{ Å}^2)$ through binding of furosemide at a ratio of furosemide to triamterene of 0.5:1.0. Exceeding or altering this ratio in various ways, e.g. 1:1.5 or 1:0.2 results in either unspecific binding of furosemide formation of separate micelles of different sizes with no fusion, especially in the presence of stearates, soluble polyvinylpyrolidone cellulose acetate, phthalate, etc., yielding a heterogeneity of micellar ions of uncontrolled matter of the active ingredients.

Mixed micelles formation between triamterene and furosemide, having a molar ratio of 0.5:1, specifically the retardation of furosemide, reflects the desire of the more hydrophobic side of triamterene to eliminate its contact with the aqueous solvent. Conversely, the less hydrophobic—the hydrophobic—side, found on the external surface of the triamterene micelles (the aminogroups, the possible covalently water addition at position 5 and 6), governs the stability and completing of the mixed micelles of triamterene and furosemide, in the presence of stearate, phthalate, etc., surface properties, e.g. surface lowering tension, collapse pressure, equilibrium spreading, and HPLC mobilities and dissolution rates, and all of these characteristics appear to correlate more or less with the furosemide—solubilizing property of triamterene.

Figure 10:
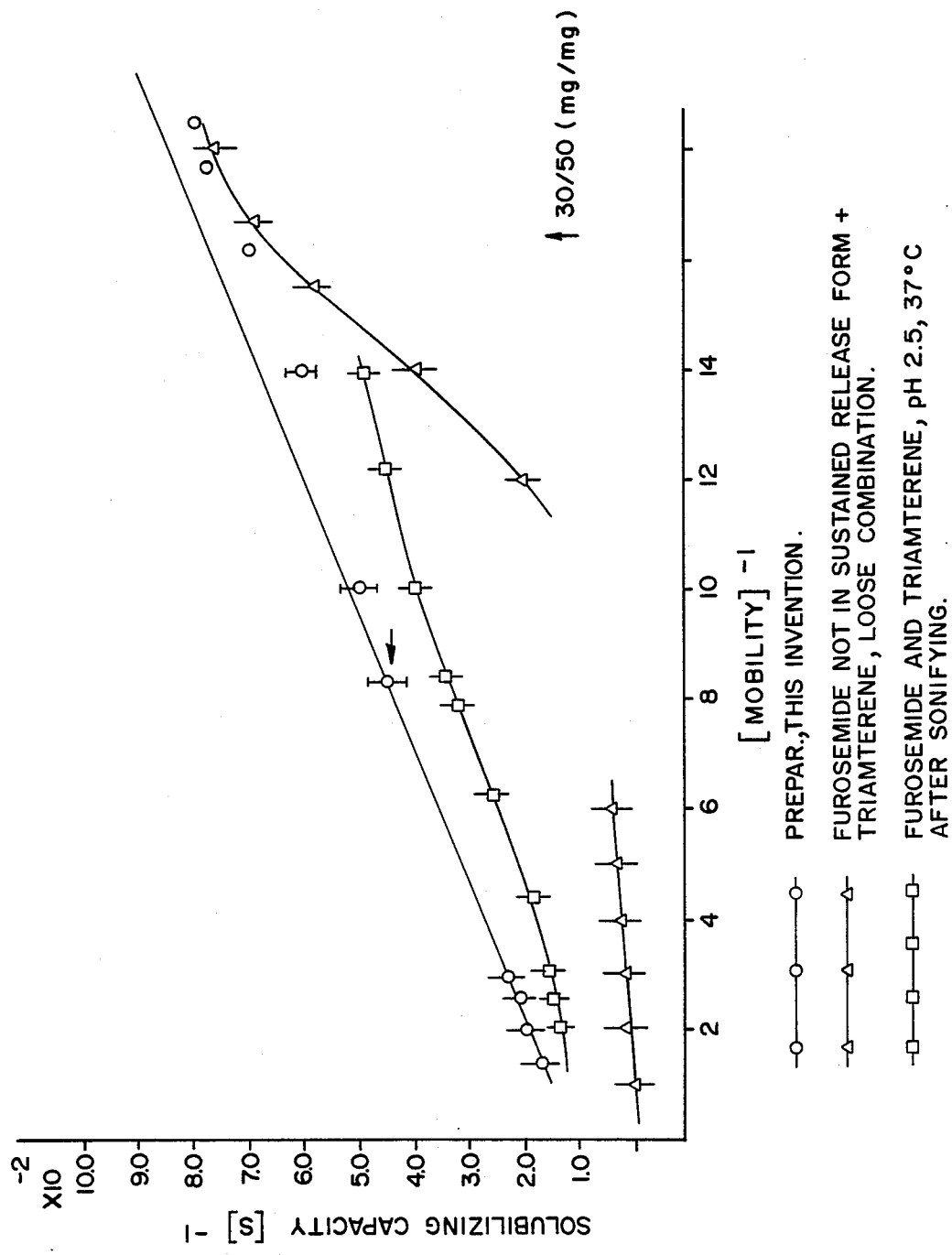
FIG. 10—Solubilizing capacity $[S]^{-1}$ vs. hydrophilicity according to this invention and other loose combinations.

HPLC—Properties:

The solubilizing capacity ($S^{-1}$), where S means the ratio of moles of furosemide per mole of triamterene vs. the normalized retention times (mobility $^{-1}$) when measured by reversed phase high performance liquid chromatography (HPLC) discloses the furosemide-solubilizing capacity of triamterene. The correlation between furosemide solubilizing capacity and HPLC-mobility is quite unexpected and striking, in that the faster the furosemide or furosemide anion mobility at pH>7.0<9.5 by HPLC, e.g. higher concentrations of furosemide in the claimed combination, the lower the triamterene-solubilizing capacity. In contrast, the slower the mobility (or greater the reduction) by HPLC, e.g. triamterene at various concentrations without furosemide, the larger the furosemide-solubilizing capacity up to a maximum of a ratio of furosemide to triamterene of 0.5:1.0. This relationship is also preserved when $S^{-1}$ and (HPLC-mobility are plotted at different pH's than 2.5, and is also valid in the range between pH 1.5 to 9.5 (37° C.). (FIG. 10)

The results for equilibrium furosemide solubilities in triamterene/salt mixtures (0.15M) and 37° C. reveal a number of striking differences between furosemide and furosemide in controlled release forms, e.g. in a pharmaceutical formulation with stearates, compared with furmosemide at different ratios of furosemide/triamterene. First, triamterene micelles whether at pH 1.5 or in coated form, solubilize more than 10 times more furosemide in controlled release form than not in controlled release form as long as the molar ratio of furosemide to triamterene is 0.5:1. Second, the free salts of furosemide at neutral pH to basic pH, where furosemide exits mainly as anion, solubilize less furosemide than the conjugated acid which, in turn, solubilizes more furosemide when in controlled release form. On a molar basis 298, 320, 324 triamterene molecules are required to solubilize furosemide and furosemide in controlled release form, compared with 130, 350 and 360 molecules in the case of the conjugated acid and 320–350 molecules in controlled release form of furosemide at basic pH, respectively. Furthermore, these results for equilibrium furosemide solubility in triamterene are not at variance with the dissolution rates of furosemide in controlled release form and the release of triamterene using the dissolution apparatus of Dahlhausen et al. The ordering and magnitude of those equilibrium results, however, are in close agreement when calculating the release of the active ingredients molar basis obtained by dissolution of radio- labelled furosemide in combination with triamterene. (See also FIG. 4).

Table III shows the solute permeability of ions in $mols^{-1}.N^{-1}$ in the presence of furosemide and triamterene as a control, and the loose combinations in comparison to the fixed one with the constant molar ratio of 1:2 in which furosemide is in a form of controlled release. The significance of these data, especially for the fixed molar ratio of 1:2 is enhanced because the concentrations at which the complete liquid membranes according to Bhise et al. (J. Pharm. Sci. 73, 1579, 1984) are generated with the supporting membrane during the experiments are of the order of $\mu M$ and are comparable with the drugs in the renal tubules as well as in the serum of the blood (pharmacokinetics). Furthermore, an examination of Table III shows that the resistance to the transport of chloride ions and that of the potassium ion according to this invention is maximal when (i) the molar ratio is 1:0.5, (ii) furosemide is in the form of a controlled release and (iii) showing the additional effect of sparing potassium and eliminating chloride. The decrease in absorption of chloride, potassium and sodium by the combination of this invention having a molar ratio of furosemide to triamterene of 1:2 is accompanied by a decrease in re-absorption of water which results in diuresis possibly as a consequence of modification in the permeability of ions. The balance between impedance of $K^+$ and $Na^+$ ions as well as $Cl^-$ and dry administration of this combination according to the invention, is released to the molar ratios of furosemide and triamterene revealing maximal effects at a ratio of 1:2 rather nonstoichiometric molar ratios. Furthermore, according to the data of Table III it is quite unexpected that this described effect on the impedance of ions is bound to a combination of a form of controlled release in the case of furosemide, acting more or less as a remote control of release through triamterene. However, exceeding the molar ratio of furosemide to triamterene according to this invention of 1:2 to say 1:3, 1:4 etc., it is evident from Table III that no further impedence of ions will be achieved, however, slight disturbances of the impedance of chloride reabsorption will occur. These unexpected findings are consistent with the above stated experiments indicating the formation of micelles of triamterene and furosemide whereby the latter has to be in a controlled release form which is controlled remotely by triamterene in order to form mixed micelles of uniform size, molecular weight distribution and aggregational numbers. Therefore, the maximum ratio for having a narrow size distribution of these mixed micelles in solution for a suitable pharmaceutical preparation for achieving the desired medicinal effects, e.g. delayed diuresis, magnesium and calcium neutrality and not severe disturbances on the angiotensin-renin system including the regulation through aldosterone, will be two. Above a ratio of two, one receives undesired side effects because the drugs act separately not synergistically, below that they are not very active and in a pharmaceutical sense they are heterogeneous.

TABLE III

Solute Permeability in mol · s$^{-1}$ · N$^{-1}$ of Ions In The Presence of Furosemide, Triamterene and loose Mixtures of Furosemide/ Triamterene as well as of the Invented Combination of constant molar ratio On Artificial Membranes.

| | A | B | control (no drug) |
|---|---|---|---|
| $c_{Fu.}$ = .25 mM | Furosemide (mol · s$^{-1}$ · N$^{-1}$) | | |
| (Na) Cl | 250,7 ± 40,0 | 180,0 ± 40 | 430,0 ± 45 |
| $c_{Tria}$ = .30 mM | Triamterene mol · s$^{-1}$ · N$^{-1}$) | | |
| K (Cl) | 170,3 ± 10,0 | 90,5 ± 5,0 | 360,5 ± 9,0 |
| Na (Cl) | 111,2 ± 12,0 | 207,4 ± 8,0 | 245,3 ± 6,0 |
| c = 0,20 mM | Furosemide/Triamterene(0.5:1)$^X$mol · s$^{-1}$ · N$^{-1}$) | | |
| Na (Cl) | 145,3 ± 10,0 | 160,0 ± 20,0 | 450,0 ± 50 |
| K (Cl) | 120,3 ± 20,0 | 130,0 ± 20,0 | 360,0 ± 10,0 |
| (Na) Cl | 100 ± 30,0 | 110,0 ± 30,0 | 430,0 ± 45 |
| c = 0,20 mM | Furosemide/Triamterene(0.5:1)$^{XX}$(mol · s$^{-1}$ · N$^{-1}$) | | |
| Na (Cl) | 240,5 ± 30,0 | 200,0 ± 40,0 | 250,0 ± 6,0 |
| K (Cl) | 160,3 ± 20,0 | 180,0 ± 30,0 | 360,0 ± 40,0 |
| (Na) Cl | 300,0 ± 20,0 | 280,0 ± 30,0 | 420,5 ± 30,0 |
| c = 0,20 mM | Furosemide/Triamterene(1:1)$^{XX}$(mol · s$^{-1}$ · N$^{-1}$) | | |
| (Na) Cl | 270,0 ± 30,0 | 250,0 ± 40,0 | 420,0 ± 40,0 |
| K (Cl) | 159,3 ± 25,0 | 180,0 ± 30,0 | 360,0 ± 10,0 |
| Na (Cl) | 200,0 ± 30,0 | 170,0 ± 40,0 | 250,0 ± 6,0 |
| C = 0,20 mM | Furosemide/Triamterene 1:3 (1:4)$^{XX}$(mol · s$^{-1}$ · N$^{-1}$) | | |
| (Na) Cl | 300,0 ± 30,0 (290,0 ± 20,0) | 210,0 ± 40,0 (220,0 ± 40,0) | 410,0 ± 20,0 |
| K (Cl) | 160,0 ± 30,0 (150,0 ± 35,0) | 180,0 ± 30,0 | 360,0 ± 10,0 |
| Na (Cl) | 250,0 ± 30,0 (260,0 ± 30,0) | 290,0 ± 35,0 (280,0 ± 40,0) | 420,5 ± 30,0 |
| c = 0,20 mM | Furosemide/Triamterene (20 mg/80 mg$^X$(mol · s$^{-1}$ · N$^{-1}$) | | |
| (Na) Cl | 150,0 ± 30,0 | 160,0 ± 30,0 | 430,0 ± 45,0 |
| K (Cl) | 160,0 ± 20,0 | 140,0 ± 20,0 | 360,0 ± 10,0 |
| Na (Cl) | 90,0 ± 30,0 | 100,0 ± 30,0 | 250,0 ± 6,0 |
| c = 0,20 mM | Furosemide/Triamterene (80 mg/100 mg)$^X$(mol · s$^{-1}$N$^{-1}$) | | |
| (Na) Cl | 270,5 ± 30,0 | 250,0 ± 35,0 | 430,0 ± 45,0 |
| K (Cl) | 170,0 ± 20,0 | 150,0 ± 20,0 | 360,0 ± 10,0 |
| Na (Cl) | 80,0 ± 10,0 | 70,0 ± 15,0 | 250,0 ± 6,0 |

A and B the different compartments of the transport cell according to Blise et al., J. Pharm. Sci. 73, 1579, (1984).
$^X$Combination of furosemide and triamterene, where furosemide is not in a form of sustained release, however, having the same ratio as the invented combination
$^{XX}$Combination of furosemide and triamterene, where the furosemide is in a form of sustained release according to the invention Concentration used for measuring the impedence of ions.

It has been found in in vitro tests that only those preparations revealing optimum effects of furosemide binding to triamterene as stated above, according to FIG. 5 with the amount of release of active ingredients, furosemide and triamterene, determined separately by analytical methods which are maintained in the in vitro (dissolution rate) in the claimed pH-ranges are effective.

The in vitro measurements for determining the release of the active pharmaceutical ingredients of the claimed combination were performed in the "flow-through-cell" as described by Dibbern et al., Pharmazeutische Zeitung 48: 1848–1853. The aqueous buffer solution at pH 1.5 consists of 0.2 g NaCl per liter and the equivalent amount of 2N HCl, the pH's pH 2.5, pH 3.5, 5.5 and 7.5 were adjusted with equivalent amounts of disodium/sodium dihydrogen phosphate (Na$_2$HPO$_4$/NaH$_2$PO$_4$) at a concentration of 1.403 g per liter. In order to have in vivo test conditions the measurements are made at 37° C.

The controlled low release of furosemide (30 mg) in combination with triamterene (50 mg) is shown in FIG. 4. As shown in FIG. 4 a constant release of furosemide of not more than about 1.5% in about one hour in the pH range of 1.5 to 3.5 and a slow release of not more than 4.5% at pH 5.5 has been found with a concurrent release of 63% triamterene and 80% triamterene, respectively, after 100 minutes and with a release of furosemide to greater than 85% at pH 7.5 after 8 hours. This very low release of furosemide which is being controlled by the release of triamterene due to formation of mixed micelles consisting of one mol of furosemide and two moles of triamterene according to the chemical and physical characterization, lies within the therapeutic range desired.

Moreover, surprisingly by this combination the separation of magnesium and calcium is clearly reduced versus furosemide, an effect which is of special importance with long-term treatment since a lack of these electrolytes may lead inter alia to muscular cramp, e.g. systemma, tentany.

As is well known, abrasive diuretics such as furosemide very strongly stimulate the plasma-renin-aldosterone system due to the strong loss of salt and the volume changes. This undesirable reaction could surprisingly be substantially reduced by this combination. (FIGS. 10 and 11).

The two active ingredients are preferably combined in gelatine capsules and are preferably present in these capsules as granulate or as pellets.

The controlled release form of the furosemide can be done in the manner known per se, e.g. by coating the active ingredient with suitable polymers or by processing into an embedded compound. Especially useful are salts of stearate, phthalate as well as polyvinylpyrrolidone or mixtures with stearate and phthalate. Also possible is the use of microencapsulation of the furosemide or the preparation of hydrocolloid matrix tablets, or pellets.

Although the combination of the active ingredients is primarily applied in a hard gelatine capsule, other oral forms of administration are also possible. Thus in the manner known per se paraplastic shaped bodies (tablets or pills) can be used, but also drinkable suspensions as well as suppositories which can be made by the conventional known process. Apart from the active ingredients, there are also the conventional excipients such as e.g. talc, colloidal silicon dioxide, gum arabic, lactose, starch, cellulose powder, magnesium stearate and the like. Lastly, it is also possible to provide further active ingredients in the combination according to the invention.

A medicinal application of the low dosage form of this invention, e.g. 15 mg furosemide in a form of controlled release and 25–30 mg of triamterene, yield excellent results of elimination of edemas in case of long treatments without loss of magnesium or potassium. Because of the protracted and mild diuresis this low dosage formulation is suitable for the light cases of hypertension. Furthermore, this low dosage form when assigned to patients with venous edemas it can be concluded that patients with molibizable fluid in the edemas and without restriction of liquid supply no hemoconcentration with a deterioration of the flow properties of the blood will occur. Therefore, no thromboembolic diseases are to be expected from the low dosage form of this invented combination.

The invention will be described in greater detail in conjunction with the following specific examples.

EXAMPLE 1

A gelatin capsule, size 3 is filled with 30 mg of furosemide pellets in controlled release form and 50 mg triamterene pellets in non-controlled release form.

The furosemide in controlled release form is prepared in the following way:

2 kg of normal commercial pellets of 0.6 to 0.7 mm in diameter are sprayed by means of the immersion technique in a rotatory coating pan with a suspension consisting of:

| | |
|---|---|
| furosemide | 1.68 kg |
| soluble polyvinylpyrrolidone | 0.1 kg |
| talcum | 0.1 kg |
| isopropanol | 7.00 kg |
| water | 7.00 kg |

After the pellets have been dried a 5% alcoholic shellac solution or optionally a 5% alcoholic solution of cellulose acetate phthalate or a 2% alcoholic solution of hydroxypropylmethyl cellulose is applied. The procedure is terminated when the active substance furosemide is released from the pellets in the manner claimed. The release in vitro of furosemide yielded the following values:

pH 1.5: after 75 minutes, in the average 1.5% and is constant in the pH range 1.5 to 3.5 within 75 minutes.
pH 5.5 a release of not more than 4.5% after 100 minutes.
pH 7.5: a release of 90% after 8 hours.

The triamterene pellets in non-controlled release form are prepared as follows:

2 kg of normal commercial pellets of 0.6 to 0.7 mm diameter are sprayed by means of the immersion technique in a rotatory coating pan with a suspension consisting of the following substances and then dried:

| | |
|---|---|
| triamterene | 1.3 kg |
| soluble polyvinylpyrrolidone | 0.055 kg |
| talcum | 0.1 kg |
| isopropanol | 2.75 kg |
| water | 2.75 kg |

The final release of furosemide in the above mentioned controlled release form within the gelatin capsule, size 3, yielded the following data:
pH 1.5: a release of furosemide, not more than 1.0%, in the average 0.9%, within the pH range 1.5 to 3.5 after 75 minutes, concurrent with a release of triamterene of 60% within the pH range 1.5 to 3.5.
pH 5.5: a release of furosemide of not more than 4.0% after 100 minutes; concurrent with a release of triamterene of 70–75%.
pH 7.5: a release of furosemide of >85% after 8 hours, concurrent with a release of triamterene of 90% to 100%.

The final hydrodynamic results are:
Contact angle: Furosemide 105 deg., triamterene 100 deg.
Hydrodynamic radius: 25.0 Å.

EXAMPLE 2

A gelatin capsule, size 3, is filled with 30 mg furosemide pellets in controlled release form and 50 mg triamterene pellets in non-controlled release form.

Furosemide in controlled release form is prepared as follows: 2 kg normal commercial pellets of 0.6 to 0.7 mm diameter are sprayed by means of the immersion technique in a rotatory coating pan with a suspension consisting of:

| | |
|---|---|
| furosemide | 1.68 kg |
| soluble polyvinylpyrrolidone | 0.1 kg |
| talcum | 0.1 kg |
| isopropanol | 7.00 kg |
| water | 7.00 kg |

After drying the pellets they are sprayed with a suspension consisting of the following:

| | |
|---|---|
| acrylic resin Eudragit ® RL 100 | 101.01 g |
| magnesium stearate | 129.5 g |
| propanediol | 12.95 g |
| 2-propanol | 2346.5 g |

The procedure is terminated when furosemide is released from the pellets in the manner claimed. The release in vitro of furosemide according to Dibbern yielded the following values:
pH 1.5: after 60 minutes, in the average 1.2% and constant in the pH range 1.5 to 3.5 within 60 minutes.
pH 5.5: a release of not more than 4.0% after 100 minutes.
pH 7.5: a release of 85% after 8 hours.

The triamterene pellets in non-controlled release form are prepared as follows: 2 kg of normal commercial pellets of 0.6 to 0.7 mm diameter are sprayed by means of the immersion technique in a rotatory coating pan with a suspension consisting of the following substances and then dried:

| | |
|---|---|
| triamterene | 1.3 kg |
| soluble polyvinylpyrrolidone | 0.055 kg |
| talcum | 0.1 kg |
| isopropanol | 2.75 kg |
| water | 2.75 kg |

The final release of furosemide in this combination in above mentioned controlled release form within the gelatin capsule, size 3, yielded the following data:

pH 1.5: a release of furosemide not more than 1.2%, in the average 1.0% within the pH range 1.5 to 3.5 after 75 minutes, concurrent with a release of triamterene of 70% within the pH range 1.5 to 3.5.

pH 5.5: a release of furosemide of not more than 4.0% after 100 minutes, concurrent with a release of triamterene of 75%.

pH 7.5: a release of furosemide of >85% after 8 hours, concurrent with a release of triamterene of 90% to 100%.

The final hydrodynamic results of this combination are:
Contact angle: Furosemide 100 deg., triamterene 100 deg.
Hydrodynamic radius: 25.0–26.5 Å.

EXAMPLE 3

A coated tablet with 30 mg furosemide in controlled release form and 50 mg triamterene (non-controlled release form) is prepared from a core consisting of:

| furosemide | 300 g |
|---|---|
| fatty acid ester of glycerin | 552.2 g |
| microcrystalline cellulose | 653.3 g |
| soluble polyvinylpyrrolidone | 18.8 g |

The mixture of drugs is homogenized in a mixer and the homogenate pressed into cores with a weight of 150 mg. The coating of the tablet is prepared from a powdered mixture consisting of:

| triamterene | 500 g |
|---|---|
| microcrystalline cellulose | 2495 g |
| magnesium stearate | 35 g |
| insoluble polyvinylpyrrolidone | 150 g |
| soluble polyvinylpyrrolidone | 120 g |

The final release of furosemide in the above mentioned formulation in vitro yielded the following data:

pH 1.5: a release of furosemide not more than 0.9% within the pH range 1.5 to 3.5 after 75 minutes; concurrent with a release of triamterene of 60% within the pH range 1.5 to 3.5.

pH 5.5: a release of furosemide of not more than 4.5% after 100 minutes, or 14% at most after 2 hours, escorted by a release of 78% triamterene.

pH 7.5: a release of furosemide of >88% after 8 hours, concurrent with a release of triamterene of 100%.

The final hydrodynamic results are:
Contract angle: Furosemide 99 deg, triamterene 97 deg
Hydrodynamic radius: 20–25.0 Å

EXAMPLE 4

A suspension of the following composition is applied to the furosemide pellets in controlled release form given in Example 1:

| triamterene | 0.722 kg |
|---|---|
| soluble polyvinylpyrrolidone | 0.031 kg |
| talcum | 0.056 kg |
| isopropanol | 1.53 kg |
| water | 1.53 kg |

The application of the aforementioned suspension is terminated when the active substances furosemide in controlled release form and triamterene in non-controlled release form are present in the pellets in the ratio of 3:5 and when both substances are released in the manner claimed.

The final release of furosemide in the above mentioned formulation in vitro yielded the following data:

pH 1.5: a release of furosemide not more than 1.2% within the pH range 1.5 to 3.5 after 75 minutes; concurrent with a release of triamterene of 70% within the pH range 1.5 to 3.5.

pH 5.5: a release of furosemide of not more than 4.5% after 100 minutes, or 8% at most after 2 hours, escorted by a release of 80% triamterene.

pH 7.5: a release of furosemide of >90% after 8 hours, concurrent with a release of triamterene of 100%.

The final hydrodynamic results are:
Contact angle: Furosemide 100 deg, triamterene 99 deg
Hydrodynamic radius: 25.0 Å ($\bar{R}_H$)

EXAMPLE 5

A coated tablet with 30 mg furosemide in controlled release form and 50 mg triamterene (in non-controlled release form) is prepared from a core consisting of:

| furosemide | 30 mg |
|---|---|
| sodium alginate | 85 mg |
| calcium phosphate | 15 mg |
| microcrystalline cellulose | 18 mg |
| magnesium stearate | 2 mg |

The mixture of drugs is homogenized in a mixer and the homogenate is pressed into cores of 150 mg. The coating of the tablet is prepared from a mixture consisting of:

| triamterene | 500 g |
|---|---|
| microcrystalline cellulose | 2495 g |
| magnesium stearate | 35 g |
| insoluble polyvinylpyrrolidone | 150 g |
| soluble polyvinylpyrrolidone | 120 g |

From this mixture and the core, tablets are produced on a tableting machine containing 30 mg furosemide and 50 mg triamterene. The coated tablets can also be processed into dragees soluble in gastric fluid or into film tablets. The final release of furosemide in the above mentioned formulation in vitro yielded the following data:

pH 1.5: a release of furosemide not more than 0.8% within the pH-range 1.5 to 3.5 after 75 minutes; concurrent with a release of triamterene of 65% within the pH-range 1.5 to 3.5.

pH 5.5: a release of furosemide of not more than 4.5% after 100 minutes, or 9% at most after 2 hours, escorted by a release Of 80% triamterene.

pH 7.5: a release of furosemide of >85% after 8 hours, concurrent with a release of triamterene of 100%.

The final hydrodynamic results are:
Contact angle: Furosemide 100 deg, triamterene 97 deg
Hydrodynamic radius: $\bar{R}_H = 22.5$ Å

EXAMPLE 6

A hard gelatin capsule is filled with a powdered mixture consisting of 30 mg furosemide in controlled release form and 50 mg triamterene in non-controlled release form.

Furosemide in controlled release form is produced by spraying 100 g of finely powdered furosemide with 2680 g of an aqueous acrylic dispersion such as is commercially available for the microencapsulation of drugs. After drying a furosemide-acrylate powder is obtained in which furosemide is microencapsulated. The resulting micro-encapsulation is such that the desired release of active substance is fulfilled according to the patent claim. The microcapsules are mixed with 1% magnesium stearate and 0.5% highly dispersive silicon dioxide and filled into the gelatin capsules with a capsule filling machine with two dosage stations via one of the dosage stations.

Triamterene in powdered form is filled into the capsules by means of the second dosage station. The triamterene powder in non-controlled release form is produced from the following:

| | |
|---|---|
| triamterene | 25 parts w/w |
| microcrystalline cellulose | 73.5 parts w/w |
| magnesium stearate | 1 part w/w |
| highly dispersive silicon dioxide | 0.5 part w/w |

The final release of furosemide in the above mentioned formulation in vitro yielded the following data:

pH 1.5: a release of furosemide not more than 0.9% within the pH range 1.5 to 3.5 after 75 minutes; concurrent with a release of triamterene of 70% within the pH range 1.5 to 3.5.

pH 5.5: a release of furosemide of not more than 4.5% after 100 minutes, or 9.0% at most after two hours, escorted by a release of 81% triamterene.

pH 7.5: a release of furosemide of >81% after 8 hours, concurrent with a release of triamterene of 100%.

The final hydrodynamic results are:
Contact angle: Furosemide 100 deg, triamterene 100 deg.
Hydrodynamic radius: $\overline{R}_H = 25.0$ Å.

What is claimed is:

1. A pharmaceutical composition in dosage unit form comprising 15-30 milligrams of furosemide in controlled release form and 25-30 milligrams of triamterene in a molar ratio of 1:1 to 1:2, said composition yielding mixed micelles in aqueous solution at pH 1.5 to 9.5 thereby providing a composition of low polydispersity and high stability, the controlled release form of furosemide being obtained by coating the furosemide with a water-dispersible inactive controlled release coating such that it provides release of the furosemide of not more than about 1.5% after about one hour at pH 1.5 to 3.5 and a slow release of not more than 4.5% at pH 5.5 concurrent with the release of triamterene of about 60-70% and 80%, respectively, after 100 minutes and with a release of greater than 85% furosemide after eight hours at pH 7.5 in salt solutions of adjusted pH, said furosemide and said triamterene being in association with a pharmaceutical carrier.

2. A composition according to claim 1 which contains 50 milligrams of triamterene and 30 milligrams of furosemide in controlled release form.

3. The method of producing antihypertensive activity in a mammal which comprises administering to said mammal an effective amount of the composition of claim 1.

4. The method of producing antihypertensive activity in a mammal which comprises administering to said mammal an effective amount of the composition of claim 2.

5. A pharmaceutical oral composition in controlled release dosage unit form comprising 15-30 milligrams of furosemide, coated with an inactive ingredient comprising a water-diffusable controlled release coating, and additionally containing 25-50 milligrams of particles of triamterene in pellet form where the triamterene is located at the external surface area of the particles where the triamterene is adhered to the pellets by the same inactive ingredient as for furosemide, the molar ratio of furosemide to triamterene being 1:1 to 1:2 in one capsule.

6. A composition according to claim 1 in that it provides release of free furosemide of not more than about 1.5% after about one hour at pH 1.5 to 3.5 in the presence of triamterene, and a slow release of not more than 4.5% at pH 5.5 in the presence of triamterene which is concurrent with an average release of 60-70% and 80% of triamterene, respectively, after 100 minutes, and finally with a release of greater than 85% of free furosemide after eight hours at pH 7.5 in salt solutions of adjusted pH, said composition yielding mixed micelles in aqueous solution at pH 1.5 to 9.5 thereby providing a composition of low polydispersity and high stability, said furosemide and said triamterene being in association with a soluble pharmaceutical carrier.

7. A composition according to claim 6 which contains 50 mg of triamterene and 30 mg of furosemide as pellets in one capsule.

8. A composition according to claim 6 which contains 30 mg of triamterene and 15 mg of furosemide as pellets in one capsule.

9. A dosage form according to claim 6 where the pellets of furosemide have a size of 0.6-0.7 mm and triamterene of 0.7-0.9 mm in one capsule.

10. A dosage form according to claim 6 in which the controlled release coating of furosemide contains an inactive ingredient which prevents aggregation, micellization and supersaturation in aqueous media especially at low pH in the presence of triamterene by forming mixed micelles comprising furosemide and triamterene, by controlling the concentration of monomers of furosemide through the basic triamterene, particularly at low pH.

11. A dosage form according to claim 6 where the hydrophobic furosemide is present in an amount of between 20.0% and 89.50% calculated on the weight of the dry matter of the coating suspension including triamterene pellets in one capsule.

12. A dosage form according to claim 6 wherein the hydrophobic triamterene is present in an amount of between 15% and 89.50% calculated on the weight of the dry matter of the total coating suspension including furosemide pellets where the active ingredient triamterene is at the outside of the pellets, thereby producing a premicellar solution of high surface tension and hence a remote control release of furosemide at low and medium pH.

13. A dosage form according to claim 12 in which the controlled release of furosemide is obtained by a coating containing polyvinylpyrolidone, microcrystalline cellulose, stearate and/or phthalate.

* * * * *

UNITED STATES PATENT AND TRADEMARK OFFICE
CERTIFICATE OF CORRECTION

PATENT NO. : 4,834,982

DATED : May 30, 1989

INVENTOR(S) : Sigurd Putter

It is certified that error appears in the above-identified patent and that said Letters Patent is hereby corrected as shown below:

On the Title page, between [22] and [63] insert:

-- [30] Foreign Application Priority Date
Feb. 21, 1983 [DE] Fed. Rep. of Germany...3305935--

Signed and Sealed this

Thirty-first Day of July, 1990

Attest:

HARRY F. MANBECK, JR.

Attesting Officer

Commissioner of Patents and Trademarks